US008283138B2

(12) United States Patent
Browning et al.

(10) Patent No.: US 8,283,138 B2
(45) Date of Patent: Oct. 9, 2012

(54) METHOD FOR THE HIGH LEVEL EXPRESSION OF ACTIVE TUMOR NECROSIS RECEPTOR FAMILY MEMBER IMMUNOGLOBULIN FUSION PROTEINS

(75) Inventors: Jeffrey L. Browning, Brookline, MA (US); Konrad Miatkowski, Reading, MA (US); Werner Meier, Burlington, MA (US)

(73) Assignee: Biogen Idec MA Inc., Cambridge, MA (US)

(*) Notice: Subject to any disclaimer, the term of this patent is extended or adjusted under 35 U.S.C. 154(b) by 50 days.

(21) Appl. No.: 12/542,614

(22) Filed: Aug. 17, 2009

(65) Prior Publication Data

US 2010/0136625 A1 Jun. 3, 2010

Related U.S. Application Data

(60) Division of application No. 09/767,370, filed on Jan. 23, 2001, now Pat. No. 7,585,946, which is a continuation of application No. PCT/US99/29873, filed on Dec. 16, 1999.

(60) Provisional application No. 60/112,752, filed on Dec. 17, 1998.

(51) Int. Cl.
C12P 21/04 (2006.01)
C12P 1/00 (2006.01)
C12P 21/06 (2006.01)
C12N 1/20 (2006.01)
C12N 15/00 (2006.01)
C12N 5/00 (2006.01)
C12N 5/02 (2006.01)
C12N 15/74 (2006.01)

(52) U.S. Cl. ..... 435/70.1; 435/41; 435/69.1; 435/252.3; 435/320.1; 435/325; 435/471

(58) Field of Classification Search .................. None
See application file for complete search history.

(56) References Cited

U.S. PATENT DOCUMENTS

| 5,447,851 | A | 9/1995 | Beutler et al. |
|---|---|---|---|
| 5,541,087 | A | 7/1996 | Lo et al. |
| 5,605,690 | A | 2/1997 | Jacobs et al. |
| 5,656,272 | A | 8/1997 | Le et al. |
| 5,658,570 | A | 8/1997 | Newman et al. |
| 5,661,004 | A | 8/1997 | Browning et al. |
| 5,670,149 | A | 9/1997 | Browning et al. |
| 5,721,121 | A | 2/1998 | Etcheverry et al. |
| 5,726,039 | A | 3/1998 | Oppenheim et al. |
| 5,795,964 | A | 8/1998 | Browning et al. |
| 5,856,179 | A | 1/1999 | Chen et al. |
| 5,925,351 | A | 7/1999 | Browning et al. |
| 5,976,833 | A | 11/1999 | Furukawa et al. |
| 6,221,608 | B1* | 4/2001 | Middleton et al. ............ 435/7.1 |
| 6,312,691 | B1 | 11/2001 | Browning et al. |
| 6,403,087 | B1 | 6/2002 | Browning et al. |
| 6,669,941 | B1 | 12/2003 | Browning et al. |
| 7,001,598 | B2 | 2/2006 | Browning et al. |
| 7,030,080 | B2 | 4/2006 | Browning et al. |
| 7,060,667 | B1 | 6/2006 | Browning et al. |
| 7,255,854 | B1 | 8/2007 | Browning et al. |
| 7,294,481 | B1 | 11/2007 | Fung |
| 2002/0197254 | A1 | 12/2002 | Browning et al. |
| 2004/0198635 | A1 | 10/2004 | Browning et al. |
| 2005/0037003 | A1 | 2/2005 | Browning et al. |
| 2005/0281811 | A1 | 12/2005 | Browning et al. |
| 2006/0280722 | A1 | 12/2006 | Browning et al. |
| 2007/0116668 | A1 | 5/2007 | Browning et al. |
| 2008/0076155 | A1 | 3/2008 | Fung |
| 2009/0087403 | A1* | 4/2009 | Browning et al. ............ 424/85.1 |

FOREIGN PATENT DOCUMENTS

| EP | 0496973 B1 | 8/1992 |
|---|---|---|
| EP | 0608532 A2 | 8/1994 |
| WO | 91/00347 A1 | 1/1991 |
| WO | 94/06476 A1 | 3/1994 |
| WO | 96/39488 A1 | 12/1996 |
| WO | 97/03687 A1 | 2/1997 |
| WO | 97/04658 A1 | 2/1997 |
| WO | 97/41895 A2 | 11/1997 |
| WO | 98/17313 A2 | 4/1998 |
| WO | 98/25967 A1 | 6/1998 |
| WO | 99/53059 A1 | 10/1999 |

OTHER PUBLICATIONS

M.B. Al-Fageeh et al., Biotechology and Bioengineering, prepublication, 2005.*
H. Kaufmann et al., Biotechnology and Bioengineering 63(5):57-.*
A. Neil Barclay et al., "The Leukocyte Antigen FactsBook, 2$^{nd}$ ed." Academic Press, NY, 1997 pp. 10, 197, 400.*
Katherine A. Fitzgerald, "The Cytokine FactsBook, 2nd ed." Academic Press, NY, 2001 pp. 11, 27, 476.*
Kaufmann H, et al. Biotechology and Bioengineering 63(5):573-582, 1999.*
Merriam-Webster Online Dictionary, "composition," (2004).
Mohler, Kendall M. et al., "Suluble Tumor Necrosis Factor (TNF) Receptors Are Effective Therapeutic Agents in Lethal Endotoxemia and Function Simultaneously as Both TNF Carriers and TNF Antagonists," Journal of Immunology, vol. 151:1548-1561 (1993).
Naismith, James H. et al., "Seeing Double: Crystal Structures of the Type I TNF Receptor," Journal of Molecular Recognition, vol. 9:113-117 (1996).
Peppel, Karsten et al., "A Tumor Necrosis Factor (TNF) Receptor-IgG Heavy Chain Chimeric Protein as a Bivalent Antagonist of TNF Activity," J. Exp. Med., vol. 174:1483-1489 (1991).
Rennert, Paul D. et al., "Selective disruption of lymphotoxin ligands reveals a novel set of mucosal lymph nodes and unique effects on lymph node cellular organization," International Immunology, vol. 9(11):1627-1639 (1997).

(Continued)

Primary Examiner — Robert Landsman
(74) Attorney, Agent, or Firm — Nelson Mullins Riley & Scarborough LLP; Debra J. Milasincic, Esq.

(57) ABSTRACT

Methods for high level expression of active lymphotoxin-β receptor immunoglobulin chimeric proteins and their purification.

26 Claims, 11 Drawing Sheets

OTHER PUBLICATIONS

Rennert, Paul D. et al., "Surface Lymphotoxin a/b Complex Is Required for the Development of Peripheral Lymphoid Organs," J. Exp. Med., vol. 184:1999-2006 (1996).
Reuveny, S. et al., "Effect of temperature and oxygen on cell growth and recombinant protein production in insect cell cultures," Appl. Microbiol. Biotechnol., vol. 38:619-623 (1993).
Rudikoff, Stuart et al., "Functional antibody lacking a variable-region disulfide bridge," Proc. Natl. Acad. Sci. USA, vol. 83:7875-7878 (1986).
Sautes, Catherine et al., "Murine Soluble Fcg Receptors/IgG-Binding Factors (IGG-BF): Analysis of the Relation to FcgRII and Production of Milligram Quantities of Biologically Active Recombinant IgG-BF," Immunol. Res., vol. 11:181-190 (1992).
Scallon, Bernard J. et al., "Functional Comparisons of Different Tumour Necrosis Factor Receptor/IgG Fusion Proteins," Cytokine, vol. 7(8):759-770 (1995).
Scott, Daryl A. et al., "The Pendred syndrome gene encodes a chloride-iodide transport system," Nature Genetics, vol. 21:440-443 (1999).
Simonet, W.S. et al., "Osteoprotegerin: A Novel Secreted Protein Involved in the Regulation of Bone Density," Cell, vol. 89:309-319 (1997).
Smith, Craig A. et al., "CD30 Antigen, a Marker for Hodgkin's Lymphoma, Is a Receptor Whose Ligand Defines an Emerging Family of Cytokines with Homology to TNF," Cell, vol. 73:1349-1360 (1993).
Smith, Craig A. et al., "The TNF Receptor Superfamily of Cellular and Viral Proteins: Activation, Costimulation, and Death," Cell, vol. 76(6):959-962 (1994).
Stevenson, George T. et al., "Conjugation of Human Fcg in Closed-Hinge or Open-Hinge Configuration to Fab'g and Analogous Ligands," The Journal of Immunology, vol. 158:2242-2250 (1997).
Suda, Takashi et al., "Molecular Cloning and Expression of the Fas Ligand, a Novel Member of the Tumor Necrosis Factor Family," Cell, vol. 75:1169-1178 (1993).
Sureshkumar, G.K. et al., "The Influence of Temperature on a Mouse-Mouse Hybridoma Growth and Monoclonal Antibody Production," Biotechnology and Bioengineering, vol. 37:292-295 (1991).
Trueeb, Ralph et al., "Expression of an Adenovirally Encoded Lymphotoxin-b Inhibitor Prevents Clearance of Listeria monocytogenes in Mice," Journal of Inflammation, vol. 45:239-247 (1995).
Van Dullemen, Hendrik M. et al., "Treatment of Crohn's Disease With Anti-Tumor Necrosis Factor Chimeric Monoclonal Antibody (cA2)," Gastroenterology, vol. 109:129-135 (1995).
Ware, C.F. et al., "The Ligands and Receptors of the Lymphotoxin System," Curr. Top. Microbiol. Immunol., vol. 198:175-218 (1995).
Weickert, Michael J. et al., "Stabilization of Apoglobin by Low Temperature Increases Yield of Soluble Recombinant Hemoglobin in *Escherichia coli*," Applied and Environmental Microbiology, vol. 63(11):4313-4320 (1997).
Weidemann, Ralf et al., "Low temperature cultivation—A step towards process optimisation," Cytotechnology, vol. 15:111-126 (1994).
Williams, Richard O. et al., "Successful therapy of collagen-induced arthritis with TNF receptor-IgG fusion protein and combination with anti-CD4," Immunology, vol. 84:433-439 (1995).
Zhai, Yifan et al., "Light, a Novel Ligand for Lymphotoxin b Receptor and TR2/HVEM Induces Apoptosis and Suppresses in Vivo Tumor Formation Via Gene Transfer," J. Clin. Invest., vol. 102(6):1142-1151 (1998).
Information Disclosure Statement for Application No. PCT/US99/29873, dated Jul. 24, 2000.
International Preliminary Examination Report for Application No. PCT/US99/29873, received Mar. 27, 2001.
Aggarwal, Bharat B. et al., "Tumor necrosis factors: Developments during the last decade," Eur. Cytokine Netw., vol. 7(2):93-124 (1996).
Alderson, Mark R. et al., "Molecular and biological characterization of human 4-1BB and its ligand," Eur. J. Immunol., vol. 24:2219-2227 (1994).

Ashkenazi, Avi et al., "Protection against endotoxic shock by a tumor necrosis factor receptor immunoadhesin," Proc. Natl. Acad. Sci. USA, vol. 88:10535-10539 (1991).
Banner, David W. et al., "Crystal Structure of the Soluble Human 55 kd TNF Receptor-Human TNFb Complex: Implications for TNF Receptor Activation," Cell, vol. 73:431-445 (1993).
Baum, Peter R. et al., "Molecular characterization of murine and human OX40/OX40 ligand systems: identification of a human OX40 ligand as the HTLV0-1-regulated protein gp34," The EMBO Journal, vol. 13(17):3992-4001 (1994).
Bloemkolk, Jan-Willem et al., "Effect of Temperature on Hybridoma Cell Cycle and MAb Production," Biotechnology and Bioengineering, vol. 40:427-431 (1992).
Bork, Peer, "Powers and Pitfalls in Sequence Analysis: The 70% Hurdle," Genome Research, vol. 10:398-400 (2000).
Borth, Nicole et al., "Growth and production kinetics of human X mouse and mouse hybridoma cells at reduced temperature and serum content," Journal of Biotechnology, vol. 25:319-331 (1992).
Bowen, Michael A. et al., "Structure and Expression of Murine CD30 and Its Role in Cytokine Production," The Journal of Immunology, vol. 156:442-449 (1996).
Bowie, James U. et al., "Deciphering the Message in Protein Sequences: Tolerance to Amino Acid Substitutions," Science, vol. 247:1306-1310 (1990).
Browning, Jeffrey L. et al., "Characterization of Surface Lymphotoxin Forms, Use of Specific Monoclonal Antibodies and Soluble Receptors," The Journal of Immunology, vol. 154:33-46 (1995).
Browning, Jeffrey L. et al., "Preparation and Characterization of Soluble Recombinant Heterotrimeric Complexes of Human Lymphotoxins a and b," The Journal of Biological Chemistry, vol. 271(15):8618-8626 (1996).
Browning, Jeffrey L. et al., "Signaling through the Lymphotoxin b Receptor Induces the Death of Some Adenocarcinoma Tumor Lines," J. Exp. Med., vol. 183:867-878 (1996).
Bucay, Nathan et al., "Osteoprotegerin-deficient mice develop early onset osteoporosis and arterial calcification," Genes & Development, vol. 12:1260-1268 (1998).
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).
Chaplin, David D. et al., "Cytokine regulation of secondary lymphoid organ development," Current Opinion in Immunology, vol. 10:289-297 (1998).
Chicheportiche, Yves et al., "TWEAK, a New Secreted Ligand in the Tumor Necrosis Factor Family That Weakly Induces Apoptosis," The Journal of Biological Chemistry, vol. 272(51):32401-32410 (1997).
Chuppa, Sandra et al., "Fermenter Temperature as a Tool for Control of High-Density Perfusion Cultures of Mammalian Cells," Biotechnol. Bioeng., vol. 55:328-338 (1997).
Corcoran, Anne E. et al., "Characterization of ligand binding by the human p55 tumour-necrosis-factor receptor, Involvement of individual cysteine-rich repeats," Eur. J. Biochem., vol. 223:831-840 (1994).
Corcoran, A.E. et al., "Minimal tumor necrosis factor receptor binding protein: optimum biological activity of a truncated p55 soluble tumor necrosis factor receptor-IgG fusion protein," European Cytokine Network, vol. 9 (3):255-262 (1998).
Crowe, Paul D. et al., "A Lymphotoxin-b-Specific Receptor," Science, vol. 264:707-708 (1994).
Crowe, Paul D. et al., "Production of lymphotoxin (LTa) and a soluble dimeric form of its receptor using the baculovirus expression system," Journal of Immunological Methods, vol. 168:79-89 (1994).
Degli-Esposti, Mariapia A. et al., "Activation of the Lymphotoxin b Receptor by Cross-Linking Induces Chemokine Production and Growth Arrest in A375 Melanoma Cells," The Journal of Immunology, vol. 158:1756-1762 (1997).
Dermer, Gerald B., "Another Anniversary for the War on Cancer," BioTechnology, vol. 12:320 (1994).

Doumbou, Cyr Lézin et al., "Selection and Characterization of Microorganisms Utilizing THaxtomin A, a Phytotoxin Produced by Streptomyces scabies," Applied and Environmental Microbiology, vol. 64(11):4313-4316 (1998).

Eason, James D. et al., "Evaluation of Recombinant Human Soluble Dimeric Tumor Necrosis Factor Receptor for Prevention of OKT3-Associated Acute Clinical Syndrome," Transplantation, vol. 61(2):224-228 (1996).

Eggermont, Alexander M.M. et al., "Isolated Limb Perfusion With High-Dose Tumor Necrosis Factor-a in Combination With Interferon-g and Melphalan for Nonresectable Extremity Soft Tissue Sarcomas: A Multicenter Trial," Journal of Clinical Oncology, vol. 14(10):2653-2665 (1996).

Ettinger, Rachel et al., "Disrupted splenic architecture, but normal lymph node development in mice expressing a soluble lymphotoxin-b receptor-IgG1 fusion protein," Proc. Natl. Acad. Sci. USA, vol. 93:13102-13107 (1996).

Fanslow, William C. et al., "Soluble Forms of CD40 Inhibit Biologic Responses of Human B Cells," The Journal of Immunology, vol. 149(2):655-660 (1992).

Feldmann, Marc et al., "Anti-Tumor Necrosis Factor-a Therapy of Rheumatoid Arthritis," Advances in Immunology, vol. 64:283-350 (1997).

Flier, Jeffrey S. et al., "The Tumor Necrosis Factor Ligand and Receptor Families," Seminars in Medicine of the Beth Israel Hospital, Boston, vol. 334(26):1717-1725 (1996).

Forster, Simon J. et al., "Expression of Foreign Genes in Mammalian Cells Using an Antibody Fusion System," Molecular Biotechnology, vol. 1:251-263 (1994).

Freshney, R. Ian et al., Culture of Animal Cells, A Manual of Basic Technique, Second Edition, Alan R. Liss, Inc., New York, Chpt. 1, p. 4 (1987).

Furukawa, Kazuaki et al., "Effect of culture temperature on a recombinant CHO cell line producing a C-terminal a-amidating enzyme," Cytotechnology, vol. 26:153-164 (1998).

Giard, Donald J. et al., "Effect of Temperature on the Production of Human Fibroblast Interferon (41411)," Proceedings of the Society for Experimental Biology and Medicine, vol. 170:155-159 (1982).

Goodwin, Raymond G. et al., "Molecular and Biological Characterization of a Ligand for CD27 Defines a New Family of Cytokines with Homology to Tumor Necrosis Factor," Cell, vol. 73:447-456 (1993).

Green, Douglas R. et al., "Fas-ligand: Privilege and peril," Proc. Natl. Acad. Sci. USA, vol. 94:5986-5990 (1997).

Harrop, Jeremy A. et al., "Herpesvirus Entry Mediator Ligand (HVEM-L), a Novel Ligand for HVEM/TR2, Stimulates Proliferation of T Cells and Inhibits HT29 Cell Growth," The Journal of Biological Chemistry, vol. 273(42):27548-27556 (1998).

Hudde, T. et al., "Activated polyamidoamine dendrimers, a non-viral vector for gene trasfer to the corneal endothelium," Gene Therapy, vol. 6:939-943 (1999).

Jenkins, Nitel et al., "Temperature Control of Growth and Productivity in Mutant Chinese Hamster Ovary Cells Synthesizing a Recombinant Protein," Biotechnology and Bioengineering, vol. 42:1029-1036 (1993).

Kaufmann, Hitto et al., "Influence of Low Temperature on Productivity, Proteome and Protein Phosphorylation of CHO Cells," Biotechnol. Bioeng., vol. 63:573-582 (1999).

Kwon, Byoung S. et al., "A Newly Identified Member of the Tumor Necrosis Factor Receptor Superfamily with a Wide Tissue Distribution and Involvement in Lymphocyte Activation," The Journal of Biological Chemistry, vol. 272 (22):14272-14276 (1997).

Lee, Won-Ha et al., "Tumor Necrosis Factor Receptor Superfamily 14 Is Involved in Atherogenesis by Inducing Proinflammatory Cytokines and Matrix Metalloproteinases," Arterioscler. Thromb. Vasc. Biol., vol. 21:2004-2010 (2001).

Loetscher, Hansruedi et al., "Recombinant 55-kDa Tumor Necrosis Factor (TNF) Receptor," The Journal of Biological Chemistry, vol. 266(27):18324-18329 (1991).

Ludwig, Andreas et al., "Influence of the temperature on the shear stress sensitivity of adherent BHK 21 cells," Appl. Microbiol. Biotechnol., vol. 38:323-327 (1992).

Mackay, Fabienne et al., "Both the Lymphotoxin and Tumor Necrosis Factor Pathways Are Involved in Experimental Murine Models of Colitis," Gastroenterology, vol. 115:1464-1475 (1998).

Mackay, Fabienne et al., "Lymphotoxin but not tumor necrosis factor functions to maintain splenic architecture and humoral responsiveness in adult mice," Eur. J. Immunol., vol. 27:2033-2042 (1997).

Mackay, Fabienne et al., "Turning off follicular dendritic cells," Nature, vol. 395:26-27 (1998).

Marsters, Scot A. et al., "Identification of Cysteine-rich Domains of the Type 1 Tumor Necrosis Factor Receptor Involved in Ligand Binding," The Journal of Biological Chemistry, vol. 267(9):5747-5750 (1992).

Mauri, Davide N. et al., "Light, a New Member of the TNF Superfamily, and Lymphotoxin a Are Ligands for Herpesvirus Entry Mediator," Immunity, vol. 8:21-30 (1998).

* cited by examiner

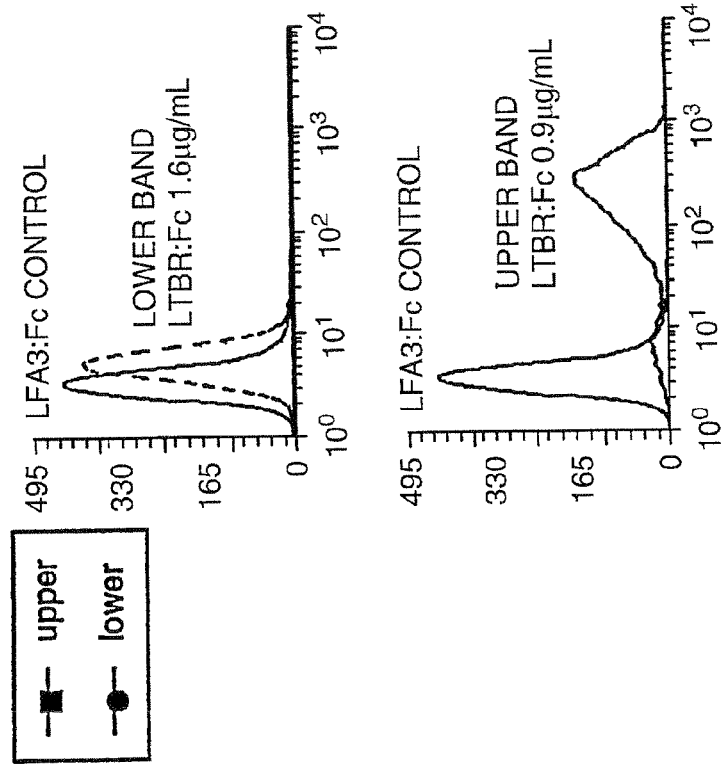
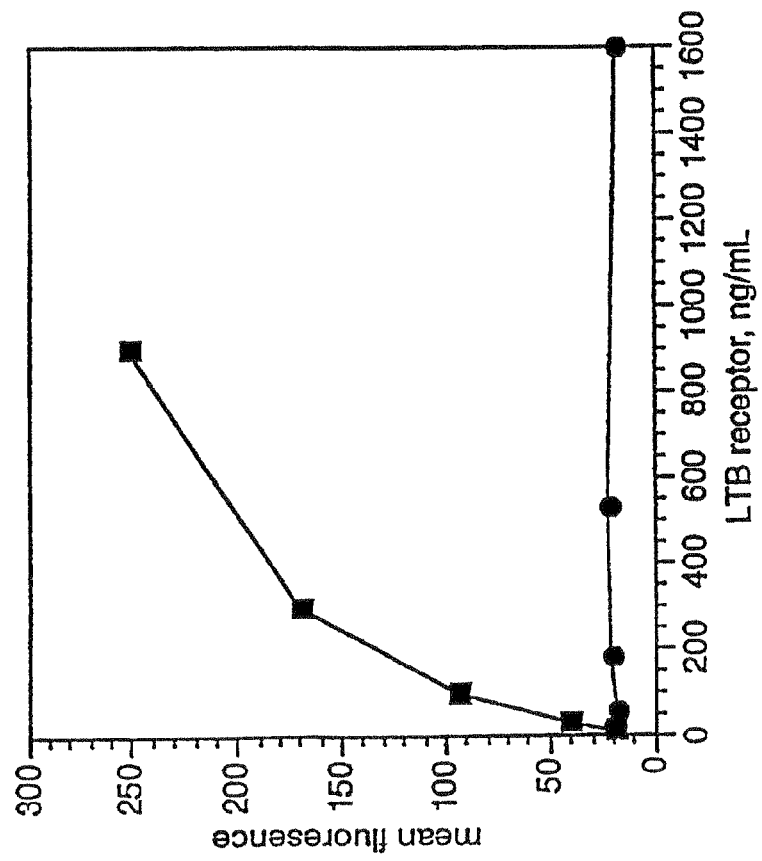
FIG. 5B
FIG. 5C
FIG. 5A

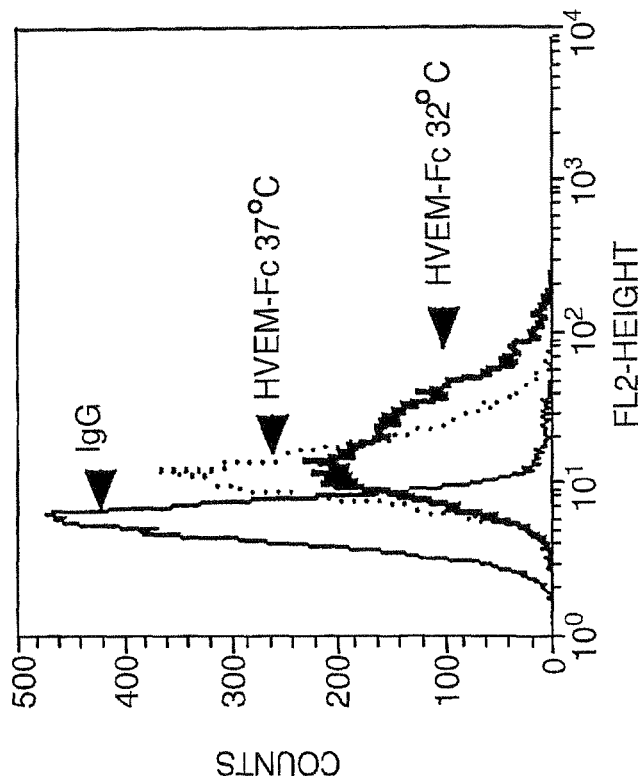
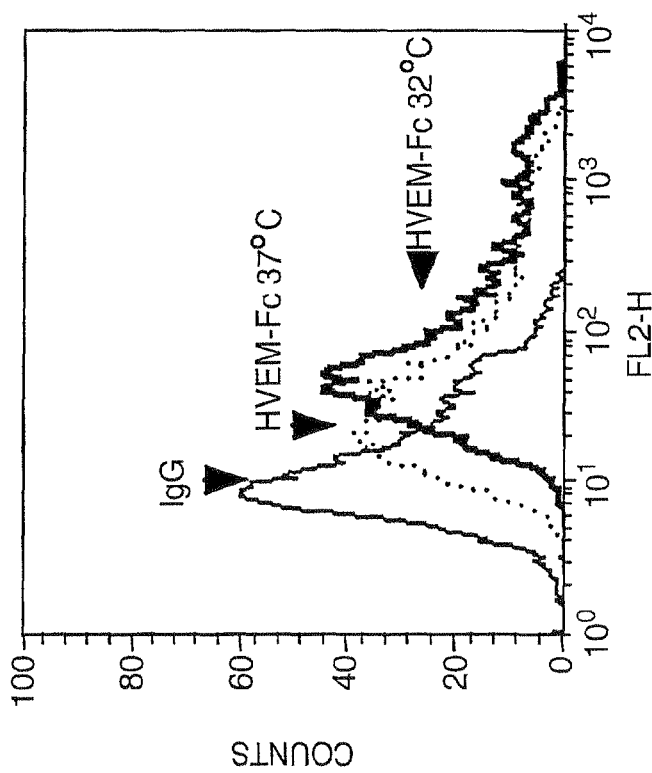

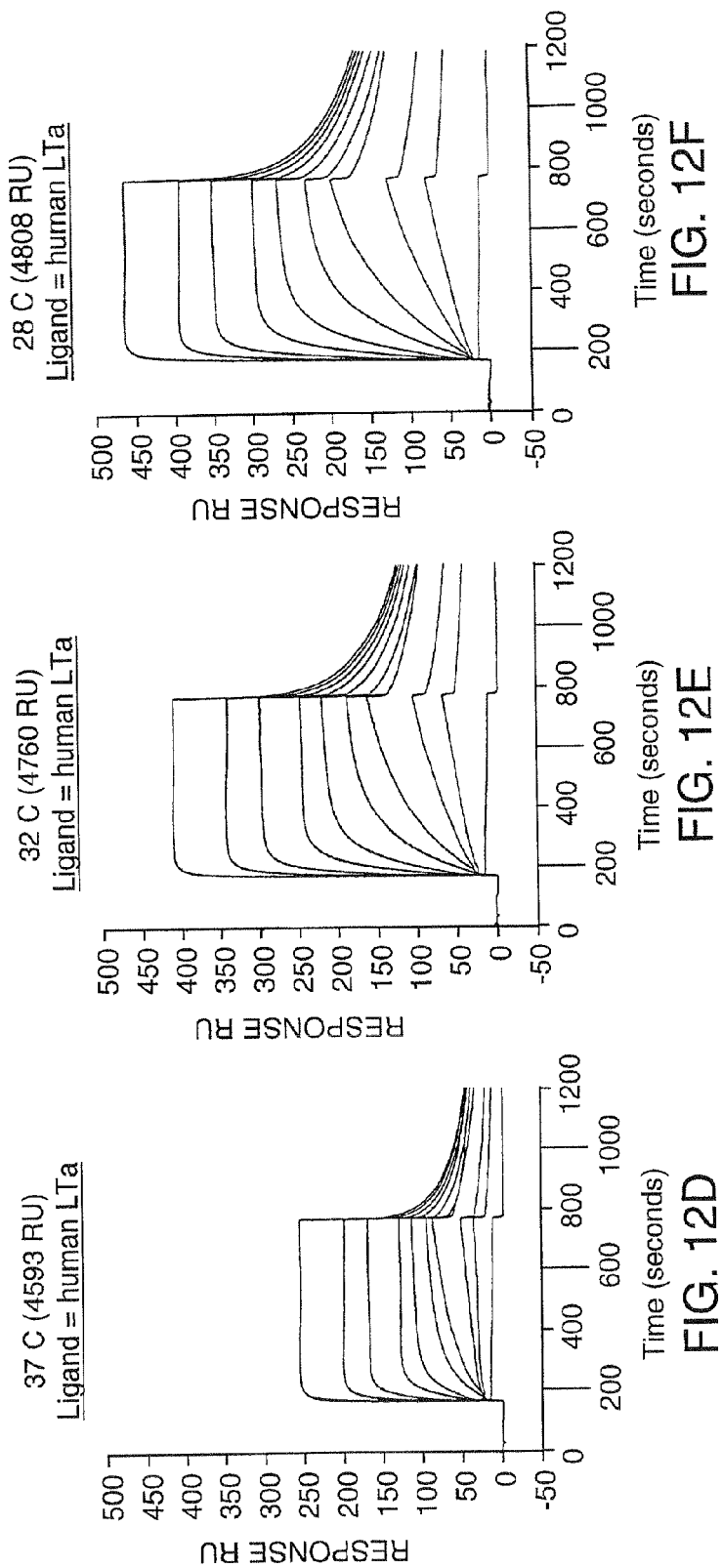

SEQUENCE LISTING

<160> NUMBER OF SEQ ID NOS: 1

<210> SEQ ID NO 1
<211> LENGTH: 258
<212> TYPE: PRT
<213> ORGANISM: Homo sapiens

<400> SEQUENCE: 1

```
Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Asp Tyr Lys Asp Asp Asp Asp Asn Gly
                 85                  90                  95

Gly Gly Ser Gly Gly Gly Ser Gly Gly Gly Ser Lys Glu Leu Asn Pro
            100                 105                 110

Ala Ala His Leu Thr Gly Ala Asn Ser Ser Leu Thr Gly Ser Gly Gly
            115                 120                 125

Pro Leu Leu Trp Glu Thr Gln Leu Gly Leu Ala Phe Leu Arg Gly Leu
        130                 135                 140

Ser Tyr His Asp Gly Ala Leu Val Val Thr Lys Ala Gly Tyr Tyr Tyr
145                 150                 155                 160

Ile Tyr Ser Lys Val Gln Leu Gly Gly Val Gly Cys Pro Leu Gly Leu
                165                 170                 175

Ala Ser Thr Ile Thr His Gly Leu Tyr Lys Arg Thr Pro Arg Tyr Pro
            180                 185                 190

Glu Glu Leu Glu Leu Leu Val Ser Gln Gln Ser Pro Cys Gly Arg Ala
        195                 200                 205

Thr Ser Ser Ser Arg Val Trp Trp Asp Ser Ser Phe Leu Gly Gly Val
    210                 215                 220

Val His Leu Glu Ala Gly Glu Glu Val Val Val Arg Val Leu Asp Glu
225                 230                 235                 240

Arg Leu Val Arg Leu Arg Asp Gly Thr Arg Ser Tyr Phe Gly Ala Phe
                245                 250                 255

Met Val
```

METHOD FOR THE HIGH LEVEL EXPRESSION OF ACTIVE TUMOR NECROSIS RECEPTOR FAMILY MEMBER IMMUNOGLOBULIN FUSION PROTEINS

RELATED APPLICATIONS

This application is a divisional of U.S. application Ser. No. 09/767,370, filed Jan. 23, 2001 which is a continuation of International Application No. PCT/US99/29873, filed Dec. 16, 1999, which claims the benefit of U.S. Provisional Application No. 60/112,752, filed Dec. 17, 1998. The entire contents of each of these applications are hereby incorporated by reference herein.

BACKGROUND

The TNF family consists of pairs of ligands and their specific receptors referred to as TNF family ligands and TNF family receptors (Bazzoni and Beutler, 1996; Aggarwal and Natarajan, 1996). The ligands such as TNF are typically found as membrane bound forms on cell surfaces, or in some cases they are selectively cleaved from the cell surface and secreted. The ligands bind to specific receptors and the binding event serves to aggregate two or more receptors. The intracellular domains of these receptors can in some way sense this change and communicate this information into the cell via a signal transduction mechanism. The family is involved in the regulation of the immune system and possibly other non-immunological systems. The regulation is often at a "master switch" level such that TNF family signaling can result in a large number of subsequent events best typified by TNF. TNF can initiate the general protective inflammatory response of an organism to foreign invasion which involves the altered display of adhesion molecules involved in cell trafficking, chemokine production to drive specific cells into specific compartments and the priming of various effector cells. As such, the regulation of these pathways has clinical potential.

The TNF receptor family is a collection of related proteins that generally consist of an extracellular domain, a transmembrane domain and an intracellular signaling domain. The extracellular domain is built from 2-6 copies of a tightly disulphide-bonded domain and is recognized on the basis of the unique arrangement of cysteine residues (Banner et al, 1993). Each receptor binds to a corresponding ligand(s) although one ligand may share several receptors. In some cases, it is clear that soluble forms of the receptors lacking the transmembrane region and/or intracellular domain exist naturally. In nature, truncated versions of these receptors may have direct biological regulatory roles. An example of this process is provided by the osteoprotegerin system. Osteoprotegerin is a secreted TNF family receptor that blocks signaling via the RANK-L (also called TRANCE) and/or TRAIL to receptors that trigger osteoclast activation. By blocking these receptors, most likely RANK receptor, bone resorption is hindered and bone mass increases (Bucay et al, 1998). Clearly, viruses have used this tactic to inhibit TNF activity in their host organisms (Smith et al, 1994). These receptors can signal a number of events including cell differentiation, cell death or cell survival signals. Cell death signaling often is triggered via relatively direct links to the cascade of caspase proteases in the case of the Fas and TNF receptors.

The TNF receptors are powerful tools to elucidate biological pathways since they are easily converted to immunoglobulin fusion proteins which have long serum halflives. Dimeric soluble receptor forms may be inhibitors of events mediated by either natural secreted or surface bound ligands. By binding to these ligands these fusion proteins prevent the ligand from interacting with cell associated receptors and inhibit the associated signal. These receptor-Ig fusion proteins are useful in an experimental sense, and have also been successfully used clinically, for example TNF-R-Ig has been used to treat inflammatory bowel disease, rheumatoid arthritis and the acute clinical syndrome accompanying OKT3 administration (Eason et al., 1996; Feldmann et al., 1997; van Dullemen et al., 1995). The manipulation of the many events mediated by signaling through the TNF family of receptors may have application in the treatment of immune based diseases as well as the wide range of human diseases that have pathological sequelae due to immune system involvement. For example, a soluble form of a recently described receptor, osteoprotegerin, has been shown to block the loss of bone mass (Simmonet et al, 1997). Thus, the events controlled by TNF family receptor signaling are not necessarily limited to immune system regulation. Antibodies to receptors can block ligand binding and thus also have clinical application. Such antibodies are often very long-lived and may have advantages over soluble receptor-Ig fusion proteins which have shorter half-lives in the blood.

While inhibition of the receptor-mediated pathway represents the most exploited therapeutic application of these receptors, originally it was the activation of the TNF receptors that showed clinical promise (Aggarwal and Natarajan, 1996). Activation of the TNF receptors can initiate cell death in the target cell and hence the application to tumors was and still is attractive (Eggermont et al., 1996). The receptor can be activated either by administration of the ligand, i.e. the natural pathway or by administration of antibodies that can crosslink the receptor. Antibodies may be advantageous for the treatment of, for example, cancers, since the antibodies can persist in the blood for long periods as opposed to ligands, which generally have short lifespans in the blood. Agonist antibodies are useful weapons in the treatment of cancer since receptors may be expressed more selectively in tumors or they may only signal cell death or differentiation in tumors. Likewise, many positive immunological events are mediated via the TNF family receptors, e.g. host inflammatory reactions, antibody production etc. and therefore agonistic antibodies could have beneficial effects in other, non-oncological applications.

Paradoxically, the inhibition of a pathway may also have clinical benefit in the treatment of tumors. For example the Fas ligand is expressed by some tumors and this expression can lead to the death of Fas positive lymphocytes, thus facilitating the ability of the tumor to evade the immune system. In this case, inhibition of the Fas system could then allow the immune system to react to the tumor in other ways now that access is possible (Green and Ware, 1997).

One member of this receptor family, the lymphotoxin-beta receptor (LTβR) binds to surface lymphotoxin (LT) which is composed of a trimeric complex of lymphotoxin alpha and beta chains (Crowe et al, 1994). This receptor-ligand pair is involved in the development of the peripheral immune system and the regulation of events in the lymph nodes and spleen in the mature immune system (Ware et al, 1995; Mackay et al, 1997; Rennert et al, 1996; Rennert et al, 1997; Chaplin and Fu, 1998). A lymphotoxin-β receptor-immunoglobulin fusion protein can be made between LTβR and IgG (LTβR-Ig) that blocks signaling between the surface LT ligand and the receptor with consequences on the functional state of follicular dendritic cells (Mackay and Browning 1998). This blocking can furthermore lead to diminished autoimmune disease in rodent models (Mackay et al, 1998, U.S. Ser. No. 08/505,606 filed Jul. 21, 1995 and U.S. Ser. No. 60/029,060 filed Oct. 26, 1996). A second member of this receptor family called HVEM for herpes virus entry mediator binds to a ligand called Light (Mauri et al, 1998) as well as the herteromeric LT ligand. The function of this receptor is currently unknown, but a HVEM-Ig fusion protein may be useful for the treatment of immunological disease and this construct has been shown to affect in vitro immune function assays (Harrop, J. A. et al, 1998).

Despite the clinical advances of members of the TNF Family as discussed above, there remains a need for a method of obtaining the desired yields of receptor Ig fusions suitable for use in a clinical setting. For example, the LTβR-Ig protein can come in two forms when expressed in either monkey cos cells or in Chinese hamster ovary cells. One form binds ligand with high affinity whereas the other does not. Therefore, there is a need for a method for producing higher yields of the form which binds with high affinity, while minimizing the presence of the lower affinity form.

SUMMARY OF THE INVENTION

The present invention relates to methods for the expression of high yields of the form of protein-Ig fusions having high affinity binding to its ligand, referred to herein as the "active" form, the form, by culturing hosts transformed with DNA encoding the desired fusions in a culture system at a low temperature thereby minimizing the amount of misfolded or misbridged protein forms. The invention in various embodiments relates to methods of expressing high yields in mammalian expression systems, by culturing transformed hosts at a temperature of about 27° C. to about 35° C. Preferably, mammalian hosts will be cultured at a temperature of about 27° C. to about 32° C.

In yet other embodiments the invention relates to methods for the expression of high yields of active fusion proteins by culturing transformed hosts in a yeast expression system at low temperatures. When the desired proteins are expressed in yeast, the preferred temperatures are from about 10° C. to about 25° C., more preferably from about 15° C. to about 20° C.

In certain methods of the claimed invention, the protein-Ig fusion comprises a member of the TNF receptor family such as a lymphotoxin-β receptor or a fragment thereof. Alternatively, the claimed methods may encompass the expression of a desired fusion protein in any expression system at low temperatures, such as an insect or bacterial system.

In other embodiments, the claimed invention encompasses the active protein-Ig fusions that are obtained by the claimed methods, and pharmaceutical compositions comprising them. In yet other embodiments, the invention relates to methods of making pharmaceutical preparations comprising culturing a host transformed with DNA encoding a desired protein-Ig fusion in a culture system having a low temperature of about 27° C. to about 35° C., preferably about 27° C. to about 32° C., to express a high yield of active fusion proteins, recovering the active protein fusions from the culture system, and combining the active fusion proteins recovered with a pharmaceutically acceptable carrier. In preferred embodiments, the protein-Ig fusion comprises a lymphotoxin-β or a fragment thereof, or HVEM, or a fragment thereof.

In still other embodiments, the claimed invention relates to pharmaceutical compositions obtained using the methods described.

The claimed invention in different embodiments relates to mammalian expression systems, as well as other expression systems, such as yeast, bacterial systems, or insect systems.

In certain embodiments, the invention relates to methods for high levels of expression of active fusion proteins in yeast, by culturing at low temperatures of about 10° C. to about 25° C., more preferably, about 15° C. to about 20° C. Active fusions obtained by this method of expression in yeast, and pharmaceutical compositions comprising these active fusions are also encompassed. Methods of making pharmaceutical preparations are encompassed within the invention comprising active protein-Ig fusions comprising culturing a yeast cell transformed with DNA encoding a desired fusion at a low temperature, preferably about 10° C. to about 25° C., more preferably about 15° C. to about 20° C. In the most preferred embodiments of all the compositions and methods of the invention, the protein-Ig fusion comprises a lymphotoxin-β receptor, HVEM, or a fragment thereof.

BRIEF DESCRIPTION OF THE DRAWINGS

FIGS. 5A-C: Ability of the flow through (lower) and eluted (upper) fractions from the AGH1 affinity column to bind to surface lymphotoxin. Mean fluorescence intensity values were derived from a FACS analysis as described. Examples of the FACS profiles are shown on the right where the LTβR-Ig is compared to the binding of a control LFA-3-Ig protein.

Figure 8:
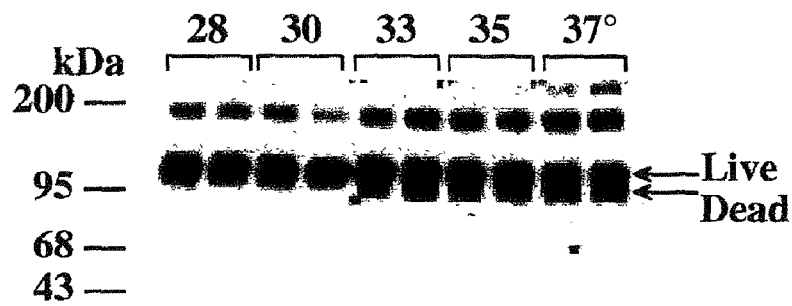

FIG. 8: SDS-PAGE/western blot analysis of human LTβR-Ig secreted from CHO cells grown at different temperatures. The CHO cell supernatants grown at the indicated culture temperatures containing human LTβR-Ig were analyzed in duplicate by nonreducing SDS-PAGE electrophoresis using 4-20% gradient gels followed by western blotting.

Figure 9:
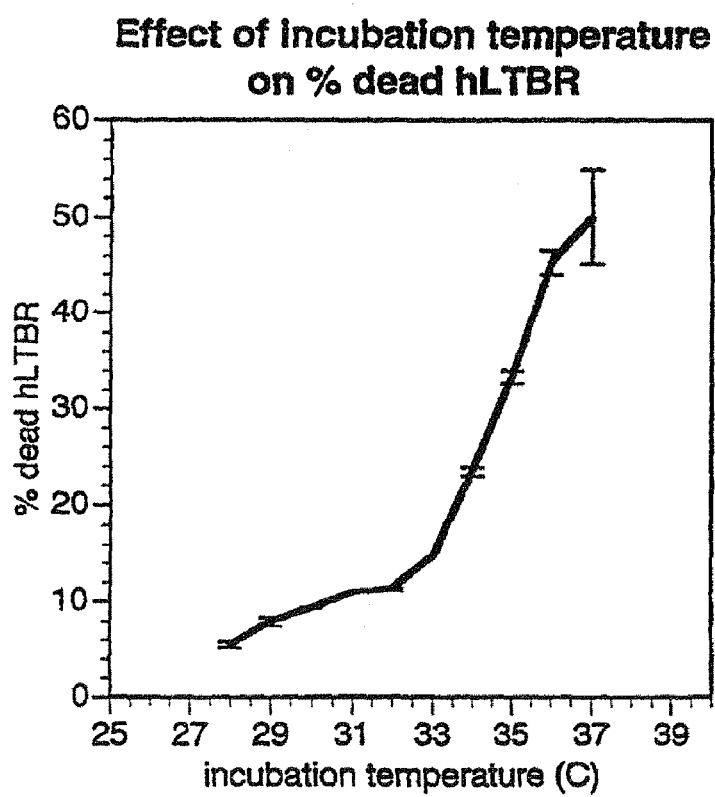

FIG. 9: Effects of culture temperature on the percentage of dead material in the total amount of human LTβR-Ig secreted from mammalian cells. Duplicate flasks containing CHO cells secreting recombinant human LTβR-Ig were cultured at the indicated temperatures and the secreted human LTβR-Ig was purified by Protein A affinity chromatography. The percentage of the "inactive" form of human LTβR-Ig was assesses in duplicate using analytical HIC chromatography. The X-axis represents the culture temperature, the Y-axis shows the amount of "inactive" material expressed as a percentage of the total amount of human LTβR-Ig secreted by the cells.

Figure 10:
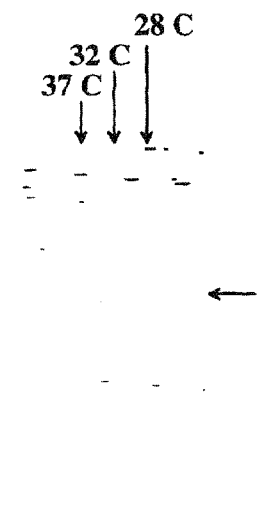

FIG. 10. Nonreducing SDS-PAGE analysis of HVEM-Ig prepared at 28, 32 and 37° C.: Protein A purified preparations of HVEM-Ig derived from cells cultured at 28, 32, and 37° C. were mixed with nonreducing SDS-PAGE sample buffer and electrophoresed on precast 4-20% SDS-PAGE gels. The protein bands were visualized with coomassie blue. The band marked with an arrow represents unaggregated HVEM-Ig. The higher molecular weight bands visible on the gel correspond to aggregated forms.

Figure 11A:
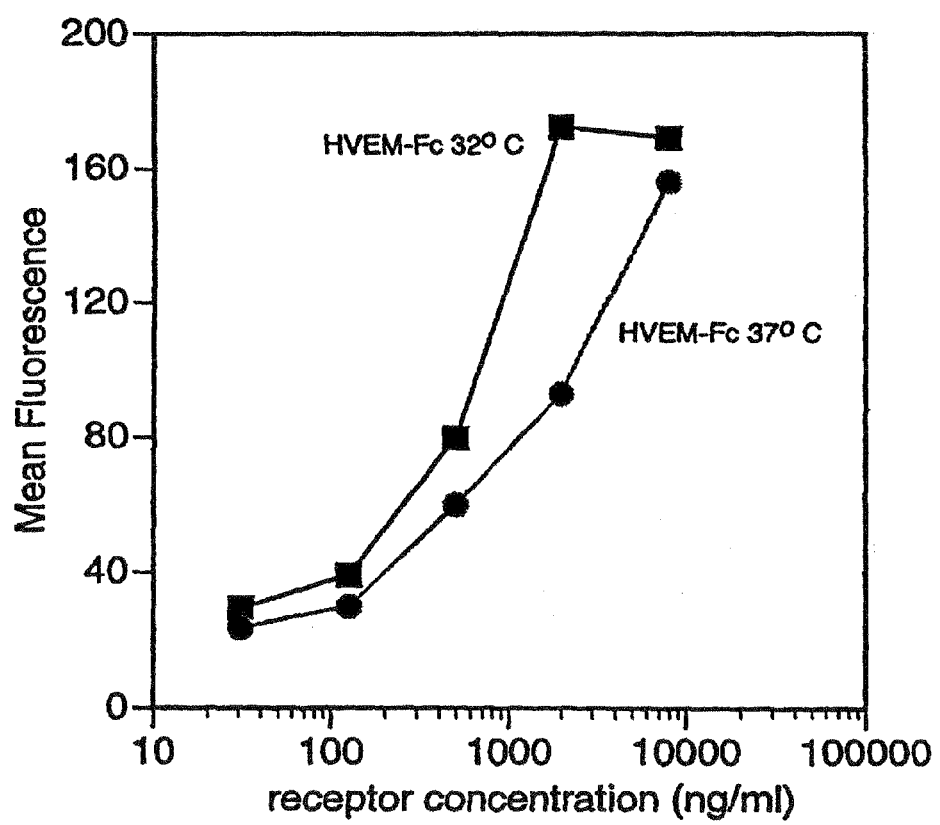
Figures 12A, 12B, 12C:
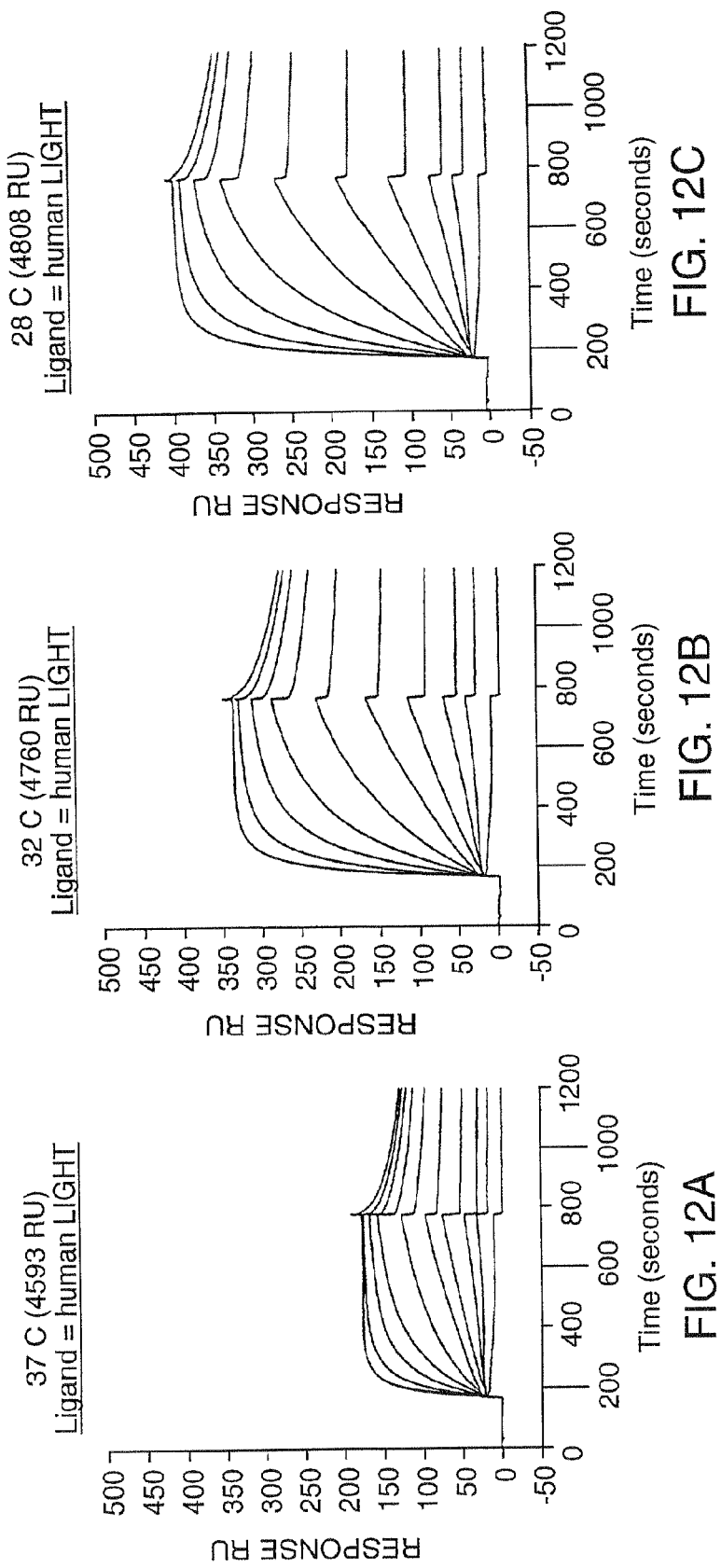

FIGS. 11A-C: FACS analysis of the binding of HVEM-Ig generated at 37° vs 32° C. to surface Light and/or LTα/β. A). Binding of HVEM-Ig as a function concentration to 293 cells transfected with human LIGHT showing that material generated at 32 C binds better than 37 material. B). An example of the FACS profiles observed of HVEM-Ig binding at a concentration of 2 ug/ml to LIGHT transfected 293 cells. C). A further example of the improved binding of 32 C generated HVEM-Ig to the surface of the II-23 T cell hybridoma line which displays both LIGHT and surface lymphotoxin-α/β (LTα/β) complex.

FIGS. 12A-F: A BIAcore analysis of the binding of either the LIGHT or lymphotoxin-α (LTα) ligands to BIA core chips immobilized HVEM-Ig generated at three different temperatures. Each curve shows a binding event at one concentration of ligand and the following concentrations were employed: 30, 15, 7.5, 3.75, 1.87, 0.93, 0.47, 0.23, 0.11 and 0.0 ug/ml. Each chip was loaded to the same RU level indicating that equal amounts of receptor-Ig were bound.

DETAILED DESCRIPTION

Reference will now be made in detail to the claimed invention. This invention concerns the ability to produce high levels of functional or active forms of immunoglobulin fusion proteins of receptors in the TNF family. The success of clinical interventions with receptor-Ig fusion proteins requires a long term presence and the ability to treat chronically or a minimum during disease flares. Ideally, preparations of such fusion proteins for human use will not have any aggregated, inactive or misfolded forms as their presence will reduce the potency of the drug and the altered structures could elicit antibody responses that may facilitate clearing of the drug thereby reducing its potency. Moreover, anti-receptor antibodies can directly cross link natural receptor on the cell surfaces thereby activating them, i.e. agonistic antibodies such as those described in Browning et al 1996, JEM. Agonistic antibodies activate the system and thus further receptor-Ig treatments may be less effective or even detrimental. By "immunoglobulin fusion proteins" we refer to any fusion of any functional portions of the extracellular domain of a polypeptide with any portion of the immunoglobulin constant regions, e.g. the CH1, CH2 or CH3 domains or combinations thereof. Preferably the polypeptide is a member of the TNF family of receptors. The portions of the Ig molecule may derive from any of the various immunoglobulin isotypes, including, for example, IgG1, IgG2, IgM, IgA etc. By "TNF family of receptors" we refer to any receptor, whether naturally membrane bound or secreted (as in the case of osteoprotegerin), which has the canonical TNF family cysteine bridging patterns or any receptor which binds to a defined member of the TNF family of ligands (e.g. Banner et al, 1993). The claimed invention in other embodiments relates to TNF family receptor-Ig fusions obtained by the methods discussed herein, as well as to pharmaceutical preparations comprising them.

LTβR-Ig protein is expressed in two forms in monkey cos cells or Chinese hamster ovary cells. One form binds ligand with high affinity, the "active" form whereas the other, the "inactive" form does not. This mixture of live and dead forms has not been described previously for any of the TNF receptor-Ig fusion proteins, however, the nature of the inactive form is not clear. The two forms were discovered by the presence of two bands in an SDS-PAGE analysis. The expressed material contains considerable glycosylation heterogeneity; however, this heterogeneity most likely does not result in the functional problems described here. For example, when the receptor is expressed as a soluble monomeric form lacking the transmembrane domain and the immunoglobulin Fc region, non-, mono- and di-N-linked glycosylated forms are observed. Both single and double glycosylated forms can be immunoprecipitated by BDA8, an antibody that recognizes only functional forms. Moreover, the affinity-purified forms have similar glycosylation heterogeneity. More likely, we speculate that the expression of a non-membrane anchored form leads to some aberrant disulfide linking resulting in inappropriate crosslinking between the two arms of the receptor-Ig dimer.

Figure 1:
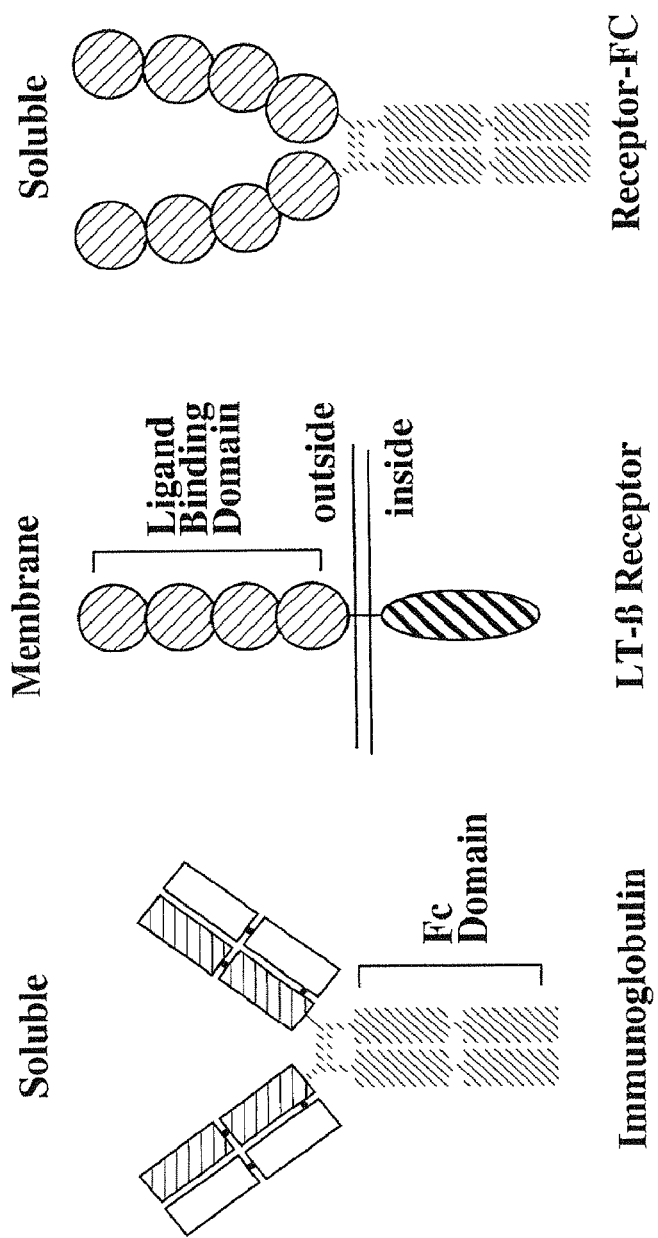
FIG. 1: Schematic of the receptor-immunoglobulin chimeric protein. The left panel shows a cartoon of a typical IgG molecule, the Fc domains are filled in black, the heavy chain variable domains are colored in gray and the light chains are left white. The middle panel contains a schematic drawing of the LTβR molecule including the intracellular (dark gray) and extracellular (light gray) domains. The right panel depicts a schematic drawing of the LTβR-Ig fusion protein.
Figure 2:
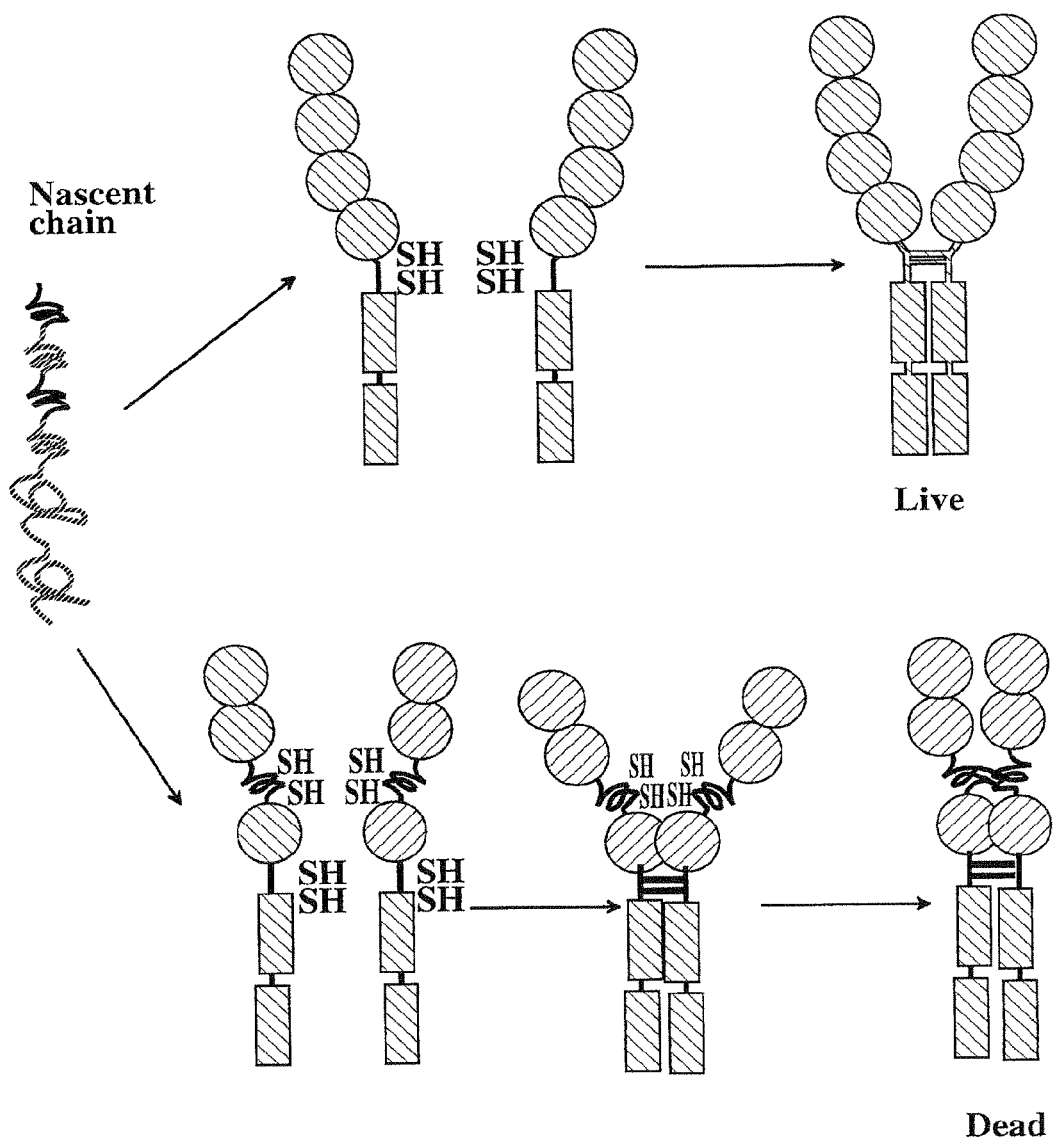
FIG. 2: Conceptual schematic showing the likely defect in the dead LTβR-Ig form, although the actual misfolded or misbridged amino acids have not been identified.
Figure 3:
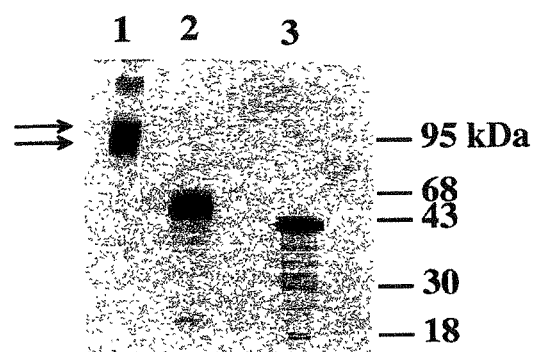
FIG. 3: SDS-PAGE analysis of human LTβR-Ig before and after treatment with PNGase F. Lanes 1 and 2 contain human LTβR-Ig purified from CHO cell culture supernatant grown at 37° C. using Protein A affinity chromatography. Lane 3 shows the same preparation after treatment with PNGase F to remove all N-linked oligosaccharides. Lane 1 is run under nonreducing conditions, lanes 2 and 3 are run under reducing conditions. The protein bands are visualized by staining the gel with Coomassie Brilliant Blue.
Figure 4:
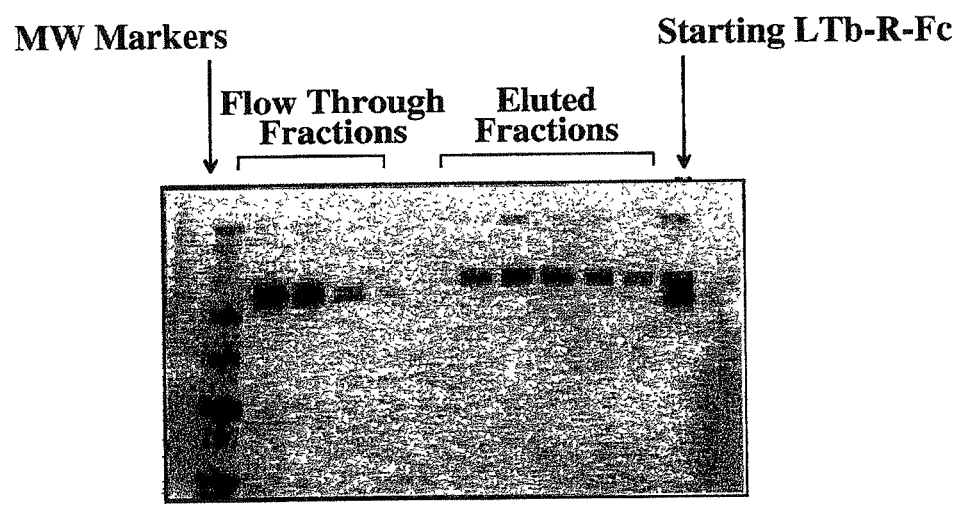
FIG. 4: A nonreduced SDS polyacrylamide gel analysis of the protein flowing through an AGH1 affinity column lanes and the protein eluted with pH 3.5 phosphate buffer. The protein before affinity purification is shown in the lane on the right side of the gel. The protein bands are visualized by staining the gel with Coomassie Brilliant Blue.

The TNF family of receptors generally 3-4 repeated domains in the extracellular ligand binding portion with about 3 disulfide bridges per domain. It is conceivable that inapproapriate folding would lead to either an incorrect pattern of disulphide bonds or the lack of some formation of disulphide bonds (illustrated schematically in FIG. 2). In the case of a receptor-Ig fusion protein, it appears that the early folding of the Fc domain enables its subsequent dimerization which brings the two LTBR chains, i.e. the two receptor arms, into close proximity. If the receptor domains have not yet completed their folding, then there is the potential for free sulfhydryls to pair between the arms, i.e. interarm bridging. Such incorrect folding may occur, or disulfide scrambling may result between free sulfhydryls juxtaposed next to already formed disulfide linkages in both cases leading to folding errors. It is also possible that incorrect folding occurs within one arm i.e. intra-arm folding errors, although such errors may not result in a radically different shape of the final molecule. In this case, active and inactive forms may not be readily resolvable using conventional sizing methods.

Lastly, in the TNFR55 receptor, the fourth domain, i.e. the domain closest to the transmembrane region has been demonstrated to be critical for ligand binding when the receptor was expressed as an Ig fusion protein (Marsters et al, 1992). This domain may be critical for many of TNF receptors. Another study on TNFR55 showed that it was critical only in the context of the Ig fusion protein, and that the membrane form lacking the fourth domain was fully active in binding TNF ligand (Corcoran et al, 1994), However, more recently, crystallographic analyses have pointed to possible critical functions associated with the fourth domain (Naismith et al, 1996). The fourth domain is relatively conserved between species yet lacks direct contacts with the ligand (Banner et al, 1993). It is possible that interarm bridging in this region between the two fourth domains which lie next to the hinge and CH2+CH3 Fc domains would not appreciably alter the global shape of the molecule and hence may be invisible in size-based separation methods. Nonetheless, this molecule would exhibit impaired ligand binding. Receptors having only 3 domains could behave in a similar fashion.

Reducing the the temperature during cell culture resulted in significantly less of the misfolded smaller form (i.e. the inactive form) being secreted. This improvement is presumably due to a reduced folding rate of the polypeptide which would allow for more time to fold the individual domains of the LTβR portion prior to assembling the receptor-Ig fusion protein into the expected dimer form. The absolute temperature required to slow down the folding process is host dependent. For mammalian cells (i.e. CHO), the claimed method preferably occurs at temperatures of about 27° C. to about 35° C., more preferably, the temperature is about 27° C. to about 32° C. Claimed methods also can be used in yeast culture systems. Yeast culture needs to be grown at temperatures of about 10° C. to about 25° C., preferably from about 15° C. to about 20° C. to achieve significant benefit.

Exploitation of the claimed invention allows the correct folding of active protein Ig fusions. It may be desirable, in some circumstances, to allow cell growth at higher temperatures, for example, about 37° C. to about 43° C., during which only a very low level of expression of the cloned gene will occur. After the desired growth period, the fusions can be expressed at the low temperatures, to produce an increased yield of active fusions. The low temperatures in mammalian systems, as discussed above, are preferably about 27° C. to about 35° C., more preferably about 27° C. to about 32° C.

Thus, the claimed methods, by lowering the temperature at which the protein-Ig fusions are expressed, allow one skilled in the art to regulate the folding of both the protein and the Ig portions of the desired protein.

Additionally, using the claimed method including affinity and/or the conventional chromatography techniques, one can now purify the active fractions sufficiently to use the chimeric proteins to block immunological function in various clinical settings. In addition, using the claimed methods having low temperature (i.e. ≦32° C. for CHO and ≦25° for yeast) cell culture conditions, it is now possible to prepare culture supernatant that is highly enriched in the larger, active form of human LTβR-Ig. Moreover, it is possible that other members of this family of receptors suffer from similar problems. For example, we see two similar bands on non-reducing SDS PAGE for the TNFR55-Ig (also called the p55 or p60 TNFR). Similarly, the properties of another TNF family receptor called HVEM are improved by secretion at lower temperatures. This receptor may form an example of an intra-arm folding error as there are no obvious size differences in the materials made at the various temperatures. Nonetheless, regardless of the mechanism, the claimed methods having results in a higher percentage of lowered secretion temperatures more active fusion proteins in preparations of the se and other member of the TNF family.

EXAMPLES

Example 1 mAb that Specifically Recognize the Live Form of Human LTβR-Ig

The LTβR-Ig protein (FIG. 1) when secreted from either COS or CHO cells transfected with a plasmid can be purified using standard protein A based affinity chromatographic methods. The purified protein consists of two closely spaced bands at about 100 kDa on a nonreducing SDS acrylamide gel (FIG. 3). The two bands differ by about 5 kDa in apparent size. When the protein is reduced, essentially two bands at about 50 kDa are resolved resulting from heterogeneous glycosylation (FIG. 3). The two bands observed under nonreducing conditions, however, do not result directly from the glycosylation differences that give rise to the pair of reduced bands. Using a panel of monoclonal antibodies to the human LTβR, we showed that antibodies from group I, i.e. AGH1 and BDA8 recognize only the large MW form of the receptor (Table I; all data except the selectivity for the upper and lower bands was taken from Browning et al, 1996). Antibodies from this group bind directly to the ligand binding region as evidenced by the observation that an Fab fragment of BDA8 can still block. Group II mAbs can also block ligand binding, however, in biological assays, these mAbs show mixed agonist and antagonist behavior. When one makes an affinity column from these mAbs (AGH1 was used in these experiments) and applies the mixture of large and small forms of the LTβR-Ig, the smaller form of the receptor flows through and the larger form sticks to the column matrix. Low pH elution yields a pure preparation of the large form (FIG. 4). The two fractions were assayed for their ability to bind to the surface phorbol ester activated II-23 T cell hybridoma cells, i.e. cells expressing surface lymphotoxin complex (as described in Browning et al, 1995), and only the fraction that bound to the mAb was able to bind to surface lymphotoxin. The flow through fraction, i.e. the lower MW band was completely inactive (FIG. 5). Specifically, supernatants from CHO cells stably transfected with the LTβR-Ig construct were passed over a protein A column to isolate the protein. Pure protein was eluted with 25 mM sodium phosphate buffer at pH 2.8 and the protein containing fractions were neutralized with 1/10 volume of 0.5 M sodium phosphate, pH 8.6. Immunoprecipitations were carried out in a volume of 0.25 ml with 3 ug of LTβR-Ig and 4 ug of anti-LTβR mAb followed by capture of the mAb with KappaLock sepharose beads which recognize only the kappa chain on the mouse mAb and not the human Fc domain. The beads were removed by centrifugation and the supernatant was cleared of remaining immunoglobulin with protein A sepharose. Beads were treated with SDS PAGE sample buffer (no reducing agent) and the buffer was loaded onto SDS-PAGE gels. Gels were run and transferred onto Hybond and western blotted with anti-human IgG Fc fragment conjugated to horse radish peroxidase (LTβR mAb followed by anti-mouse IgG-HRP and chemiluminescence detection of HRP (Amersham).

To exploit the ability of AGH1 that exclusively recognizes the active form of LTβR:Ig, an AGH1 affinity column was prepared using CNBr-activated sepharose (Pharmacia, Piscataway, N.J.) according to manufacturers protocol. The column was extensively washed with PBS and the protein A purified LTβR-Ig was applied and the flow through collected.

The column was washed with PBS and then eluted with 25 mM sodium phosphate, pH 2. Fractions containing eluant were immediately neutralized as described above. Protein concentrations were determined by absorbance at 280 nm assuming that a 1 OD solution equals 1 mg/ml. The flow-through and elution pools containing LTβR-Ig were tested for binding by FACS analysis as described (Browning et al, 1995). The flow-through fraction showed no FACS staining to cells expressing surface LT whereas the elution pool retained full binding activity.

Example 2

Figure 6:
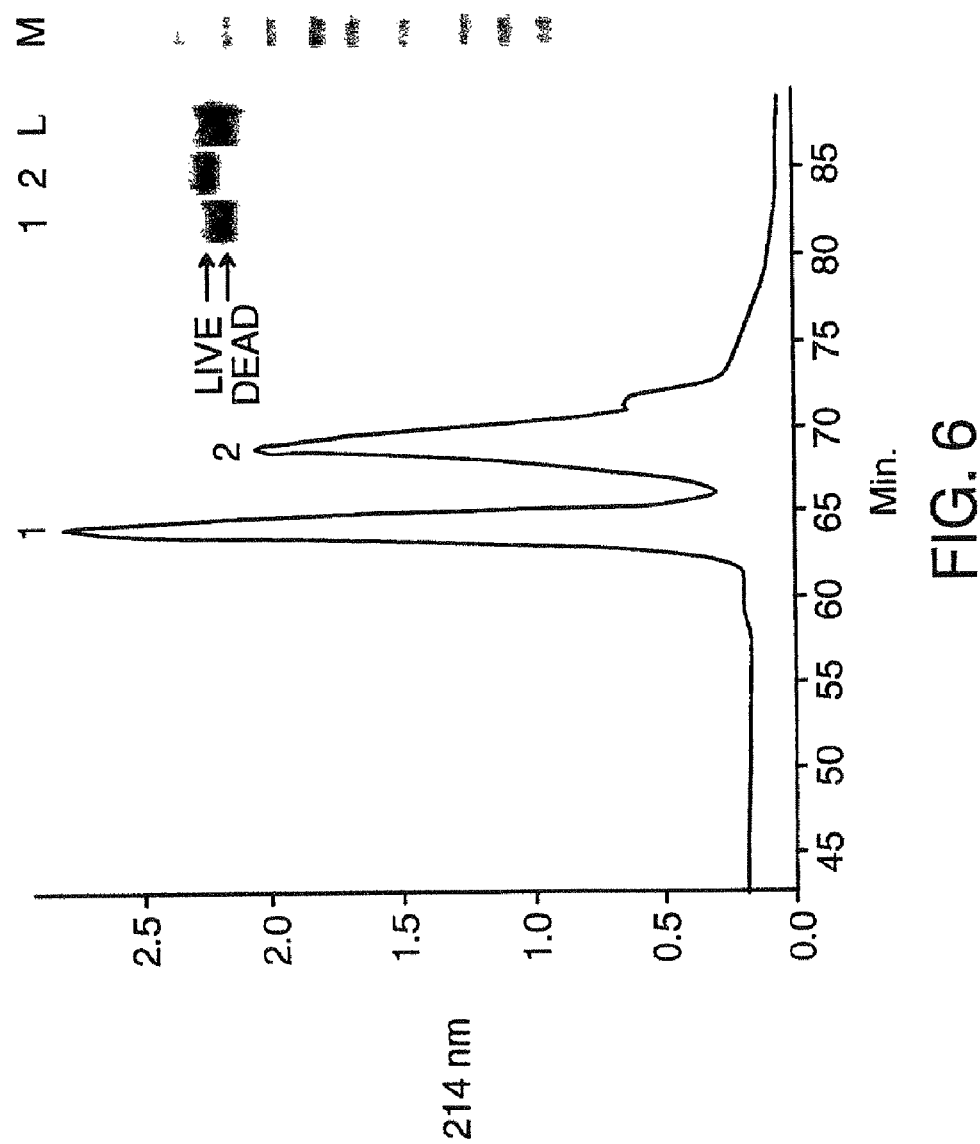
FIG. 6: Analytical HIC chromatography of human LTβR-Ig using a POROS ether column and a decreasing gradient of ammonium sulfate. Peak 1 represents the lower, inactive form, peak 2 the larger, active form of human LTβR-Ig. Fractions corresponding to peaks 1 and 2 respectively were pooled and analyzed on a 4-20% SDS-PAGE gel (inserted panel). The lane labeled "1" contains the "inactive" material from peak 1, lane 2 the "active" material from peak 2 of the HIC chromatogram. The starting material is shown in lane "L". The lane labeled "M" contains molecular weight markers.

Conventional Chromatographic Separation of Live and Dead Components of Human LTβR-Ig Potential structural differences between the large and small MW components identified above are exploited in the design of separation methods using conventional chromatography steps. As an example, the protein can be sized by gel filtration in PBS to obtain partial separation of the larger and smaller forms. These preparations can then again be applied to the same column to obtain preparations of the larger and smaller forms of human LTβR-Ig that are greater than 90% enriched in the respective components. Alternatively, hydrophobic interaction chromatography (HIC) can be employed to achieve the same result. The protein mixture is diluted with ammonium sulfate, loaded on the HIC column and the large and small components are differentially eluted with a decreasing salt gradient. Under these conditions, baseline separation of the two human LTβR-Ig components is obtained (FIG. 6). These methods as well as the imunoaffinity method described above are useful to prepare mg amounts of the large and small preparations of human LTβR-Ig but leave much to be desired for the preparation of large amounts of these components for pharmaceutical use. Applicants have invented a new method by adapting the HIC method to resins that can be obtained in bulk and have identified chromatography conditions that permit the small form of human LTβR-Ig material to flow through the column while the large component is retained and can be selectively eluted (FIG. 6). The eluted material can be subjected to a finishing step such as size exclusion or ion exchange chromatography to remove aggregated material and other impurities and, which, after formulation into a suitable physiological buffer can be used for in vivo work. The first example below (A) describes the specific conditions that were used to analytically assess the amount of inactive material in a preparation of LTβR-Ig. The second example (B) describes the preprative purification process that results in a preparation of LTβR-Ig highly enriched in the active component.

A). Analytical Hydrophobic Interaction Chromatography (HIC) can be Used as a Quantitative Assay to Assess the Amounts of Inactive LTβR-Ig Baseline resolution of the smaller, inactive and the larger, active components of recombinant human LTβR-Ig was achieved on a Perseptive Biosystems Poros ether/m column (4.6×100 mm, catalogue No. P091M526) equilibrated in 1.5 M ammonium sulfate and subsequent elution in a decreasing gradient of ammonium sulfate. The LTβR-Ig preparations were diluted to a concentration of 0.1 mg/ml and brought to a final buffer composition of 1.5 M ammonium sulfate, 20 mM sodium phosphate, pH 9 (buffer A). A portion (1 ml containing 100 μg of protein) was loaded onto the Poros ether/m column. The column was washed with 8.3 ml of buffer A. The active and inactive components were differentially eluted with a linear gradient (total gradient volume of 16.6 ml) from 100% buffer A to 100% buffer B (20 mM sodium phosphate, pH 9) followed by a 16.6 ml wash with buffer B. The column effluent was monitored for absorbance at 214 nm. The whole procedure was carried out at ambient temperature using a column flow rate of 1 ml/min. The elution profile of a representative analytical HIC chromatogram is shown in FIG. 5. Peak 1 contains the inactive fraction and peak 2 the active fraction of LTβR-Ig. In order to quantify the relative contribution of the two forms, the peak areas were integrated using the Perseptive instruments Vison integration software.

B). Preparative Purification of Human Recombinant LTβR-Ig.

Clarification and concentration of conditioned media: The cell debris was removed from 10 L of conditioned media harvested from CHO cells secreting recombinant LTβR-Ig using dead end filtration through a 5μ polypropylene 5 sqft. Calyx filter capsule (Microseparations Inc, Westborogh, Mass.) followed by a 0.2μ Opticap 4 inch filter cartridge (Millipore Corp., Bedford, Mass.). The clarified media was concentrated by ultra filtration to approximately 1 L using three S1Y30 Spiral Ultrafiltration cartridges (Amicon, Beverly, Mass.) connected in series.

Protein A affinity Chromatography: The concentrated conditioned medium was passed by gravity through a 10 ml Protein A sepharose fast flow (Pharmacia) column at 4° C. The column was washed with 50 ml of PBS, 50 ml of PBS containing 0.5 M NaCl, and 50 ml of PBS. To remove contaminating bovine IgG, the column was washed with 50 ml of 25 mM sodium phosphate, pH 5.5. The bound LTβR-Ig was eluted by gravity with 25 mM sodium phosphate, 100 mM NaCl, pH 2.8 in 3 ml fractions and immediately neutralized with 0.3 ml of 0.5 M sodium phosphate, pH 8.6. Fractions containing protein were identified by absorption spectroscopy, pooled and stored at −70° C.

Figure 7:
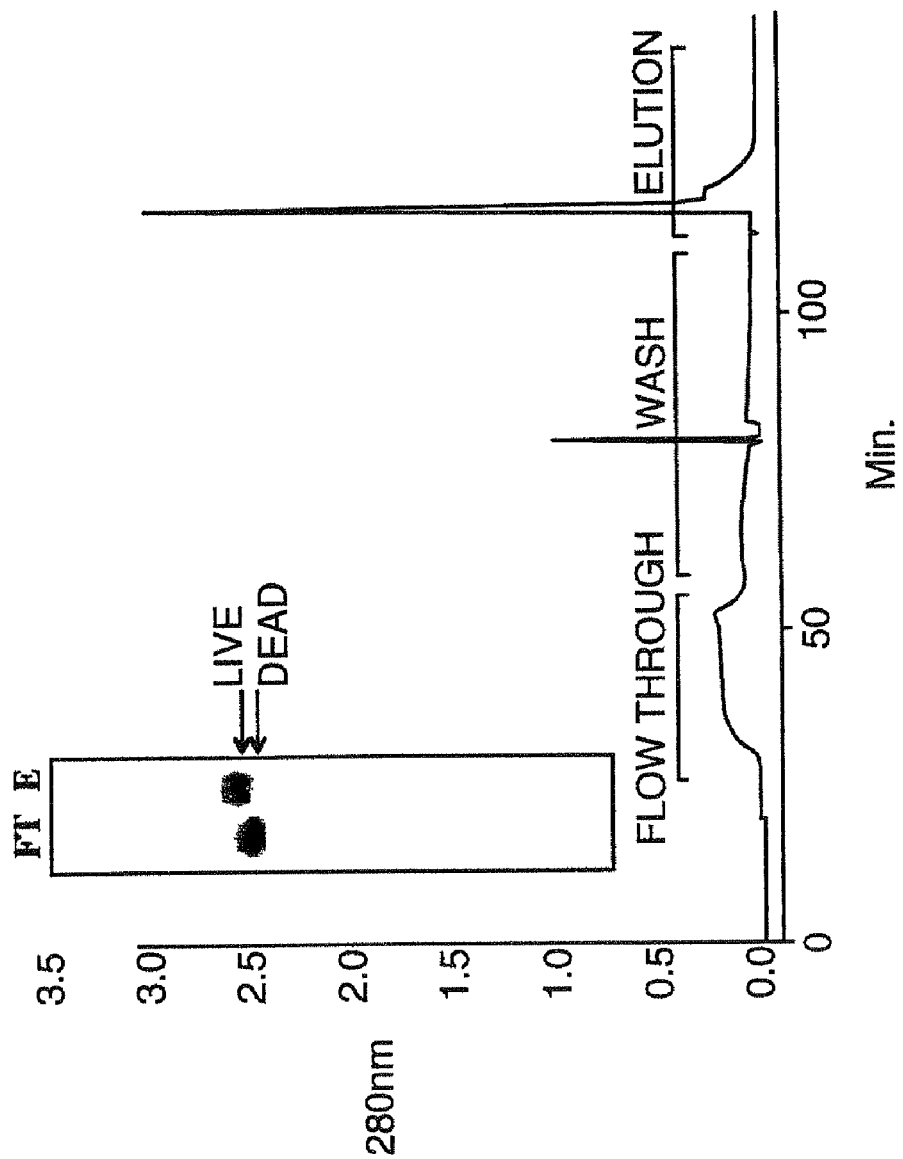
FIG. 7: Preparative HIC (hydrophobic interaction chromatography) chromatography of human LTβR-Ig using a Pharmacia Source 15 PHE column. Protein A eluate containing human LTβR-Ig is adjusted with 5 M NaCl to a final concentration of 1.5 M NaCl, 20 mM sodium phosphate, pH 7.0 and loaded onto the column. The column was washed with 5 volumes of 1.5 M NaCl, 20 mM sodium phosphate, pH 7.0 and eluted with 20 mM sodium phosphate, pH 7.0. The X-axis represents the time in minutes, the Y-axis shows the absorbance at 280 nm. Shown in the figure insert is the image of a nonreducing 4-20% SDS-PAGE gel stained with Coomassie Brilliant Blue of the flow through (FT) and elution (E) pools. The migration positions of the "live" and "dead" forms are indicated with arrows.

Hydrophobic Interaction Chromatography: The protein A elution pool (40 ml at a concentration of 2.5 mg/ml) was diluted with 40 ml of 3 M sodium chloride, 40 mM sodium phosphate pH 7 and 20 ml of 1.5 M sodium chloride, 20 mM sodium phosphate pH 7 (all solution were at ambient temperature). The diluted pool was loaded onto a 10×100 mm (7.8 ml) Source PH15 (Pharmacia, Piscataway N.J.) at a flow rate of 2 ml/min. The column was washed with 79 ml of 1.5 M sodium chloride, 20 mM sodium phosphate pH 7 at a flow rate of 20 ml/min. The bound protein was eluted with 20 mM sodium phosphate pH 7 at a flow rate of 2 ml/min. The absorbance of the effluent was monitored at 280 nm and 9 ml fractions were collected. Elution fractions containing protein were identified by UV absorption spectroscopy, pooled and stored at −70° C. FIG. 7 represents a typical HIC elution profile. Under these conditions, the inactive material flows through the column and the active material is bound to the resin. The FIG. 7 insert contains a scan of the coomassie blue stained NR SDS-PAGE analysis of the follow-through and elution pools, respectively.

Size Exclusion Chromatography: Approximately 100 ml (1.3 mg/ml) of the HIC elution pool containing the active components of LTβR-Ig were concentrated by ultrafiltration to 9 ml using a centriprep 30 concentrator (Amicon, Beverly, Mass.). The concentrate (10.3 mg/ml) was loaded onto a 1.6×100 cm Superose-6 prep grade (Pharmacia, Uppsala, Sweden) column equilibrated in PBS at a flow rate of 1 ml/min. The effluent was collected in 3 ml fractions. Fractions containing protein were identified by UV absorption spectroscopy. Selected fractions were analyzed for aggregate content at a 3 μg/lane load using NR SDS-PAGE gel electrophoresis. Fractions with minimal visible aggregate were pooled and stored frozen at −70° C.

In this fashion, LTβR-Ig can be prepared that contains minimal amounts of the inactive LTβR-Ig component that is present in the crude culture media.

Example 3

Low Temperature Fermentation Conditions Enrich for the Large, Active Component of Human LTβR-Ig During the Cell Culture Stage Under conventional mammalian cell culture conditions, human LTβR-Ig is secreted as a mixture of approximately 50% small and 50% large components. Using baculovirus infected insect cells to express the same protein results in drastically reduced levels of the small form. As insect cells are cultured at 28° C., we explored if human LTβR-Ig secreted from mammalian cells grown at low temperature would have an altered ratio of large and small forms. Shown in FIG. 8 are the supernatants from CHO cells secreting human LTβR-Ig cultured in T-flasks at 28, 30, 33, 35, and 37° C. analyzed by western blot. The large and small forms (indicated by arrows) are present in the cultures grown at 33, 35, and 37° C. Very little evidence of the small form can be seen in the lanes containing culture supernatant from cells grown at 30 and 28° C. Thus, lowering the temperature during cell culture dramatically reduces the amount of the small, inactive form of human LTβR-Ig. To quantify the relation ship between cell culture temperature and the extent of the enrichment for the larger, active form of human LTβR-Ig, duplicate culture flasks were set up and grown at temperatures ranging from 28-37° C. in one degree intervals. The protein A affinity purified human LTβR-Ig samples were analyzed by analytical HIC chromatography to quantify the ratio of the small and large components of human LTβR-Ig present in the preparations derived from cells grown at the different temperatures. As shown graphically in FIG. 9, the amount of the lower band rapidly decreases approximately 5 fold when the culture temperature is lowered from 37 to 32° C. Lowering the culture temperature to 28° C. reduces the amount of the lower form but in a much less dramatic fashion. These results show that reducing the culture temperature by only a few degrees from 37° C. dramatically decreases the amount of the smaller mw component, thus increasing the yield of the larger active component of human LTβR-Ig. Based on these data, culture temperatures of 32 and 28° C. were selected to test if these observations could be duplicated on a large scale under conditions that would be suitable for manufacturing using CHO cells secreting recombinant human LTβR-Ig that had been adapted to growth in suspension. For these experiments, the cells were grown to densities approaching $2 \times 10^6$ cells/ml at 37° C. the culture was diluted with approximately 4 volumes of growth media and incubated at 32° C. until the cell viability dropped below 80%. Lowering the temperature to 28° C. during the production phase also results in significantly lower levels of the ideadî component in the final harvest. It was interesting to note that while the cell number did not increase very much during the production phase at 28 or 32° C., a several fold increase in product titer over culture grown exclusively at 37° C. was obtained in the harvested conditioned media. The specific conditions that were used in the 32 and 28° C. process are described below.

Initial data suggests that lowering the culture temperature results in similar benefits in other host systems such as yeast. It is interesting that in yeast, the beneficial effects of low temperature production are observed at much lower temperatures than in mammalian cells. Yeast cultured at 30° C. produce predominantly the inactive form, cultures grown at 25° C. contain about an equal mixture of the inactive and active forms and cultures fermented at 16° C. produce predominately the active form of human LTβR-Ig. These observations suggest that low temperature fermentation will result in significantly higher yields of the active component of human LTβR-Ig in any secretory host system. One skilled in the art can easily determine the optimal production temperatures for each system.

Here we provide a detailed example of how this process was applied to the production of LTβR-Ig. Two cell culture methods were developed that take advantage of the fact that reducing the cell culture temperature significantly reduces the amount of the inactive components present in LTβR-Ig secreted from host cells. An additional, unexpected benefit of low temperature fermentation is a several fold improvement in titer when compared to traditional fermentation runs carried out at 36-37° C. Table II summarizes the comparative yields and the relative amounts of inactive LTβR-Ig components obtained with two different cell lines transfected with different LTβR-Ig constructs which varied in the extent of glycosylation (not germane to the thrust of this example).

32° C. Cell Culture Process: CHO cells secreting human LTβR-Ig that had been adapted to growth in suspension were grown in DME/HAM's F-12 growth media (see Table III below) supplemented with 10% FBS, 140 mg/L streptomycin, and 50 mg/L gentamycin. For scale-up, two 750 ml-spinner flasks were inoculated at approximately $2 \times 10^5$ cells/ml in growth media. The cultures were grown at 37° C. in a 5% $CO_2$ atmosphere to a density of approximately $3 \times 10^6$ cells/ml. The cell suspensions from both spinner cultures were combined to inoculate the scale-up bioreactor containing approximately 10 L of growth media. The culture was oxygenated at 11% $O_2$ and grown for three days at 37° C. to a density of approximately $2 \times 10^6$ cells/ml. This culture was used to inoculate the production bioreactor containing 33 L of growth medium at a density of $6.4 \times 10^5$ cells/ml. The production bioreactor was then cultured for 8 days at the beneficial temperature of 32° C. with the oxygen sparge rate set at 11% $O_2$. The cell density on the harvest day (day 8) was approximately $2 \times 10^6$ cells/ml with a viability of approximately 60%. Under these conditions, a titer of 12 mg/L LTβR-Ig was achieved which was two-fold higher than when the same cells were cultured at the traditional temperature of 37° C. The relative amount of the inactive component in the LTβR-Ig preparation was 17% which represented a more than 60% decrease when compared to product obtained from a 37° C. culture.

28° C. Cell Culture Process: CHO cells secreting human LTβR-Ig that had been adapted to growth in suspension were grown in DME/HAM's F-12 growth media (see table III below) supplemented with 10% FBS, 140 mg/L streptomycin, and 50 mg/L gentamycin. For scale-up, two 800 ml-spinner flasks were inoculated at approximately $2 \times 10^5$ cells/ml in growth media. The cultures were grown at 37° C. in a 5% $CO_2$ to a density of approximately $3.5 \times 10^6$ cells/ml. The cell suspensions from both spinner cultures were combined to inoculate the scale-up bioreactor containing approximately 10 L of growth media. The culture was oxygenated at 11% $O_2$ and grown for two days at 37° C. to a density of approximately $1.7 \times 10^6$ cells/ml. This culture was used to inoculate two 40 L and one 10 L production bioreactor at starting cell densities of $2.5-3 \times 10^5$ cells/ml using a split ratio of 1:9. The production bioreactors were cultured at 37° C. and oxygenated at 11% $O_2$ until a cell density of approximately $2 \times 10^6$ cells/ml was reached (two days). At the end of day two, the bioreactor temperature was lowered to 28° C. and the bioreactors were cultured for an additional 5 days. On day 7, at cell densities of approximately 3×10⁶ cells/ml and cell viability of >75%, the bioreactors were harvested and the conditioned media was processed as described above. Under these conditions, a final titer of approximately 20 mg/L LTβR-Ig was achieved which represents a 3.3 fold increase over the titer that was obtained when the same cells are cultured at 37° C. The relative proportion of the inactive component was 10% which represents a 80% decrease over the material prepared at 37° C.

Example 4

Alterations in the Fc Domain to Minimize Dead Forms During Production

Based on our hypothetical explanation of why dead molecules result in these preparations, one would predict that slowing the time before Fc domains would dimerize would increase the fraction of correctly folded receptor domains. We explored several methods to achieve this result. It is possible that different Ig Fc domains would fold at different rates, yet exchange of the IgG1 domain for an IgG4 domain did not change the live dead ratio. Secondly, the cysteine residues in hinge region that crosslink the two peptide chains were removed from the IgG1 Fc domain by mutagenesis. The Fc domains can dimerize well in the absence of hinge disulfide formation but the rate may be slower in its absence. Replacement of the two cysteine residues by alanine resulted in a decreased amount of dead form as quantitated by SDS-PAGE and HIC chromatography such that where wild type LTβR-Ig would contain 50 and 5% dead forms at 37 and 28° C., the deletion of the cysteines from the IgG1 hinge lead to 20 and 5% dead form when produced at these respective temperatures. Therefore, hinge modification by replacement of both cys residues can improve the quality of a preparation and, moreover, it is possible that replacement of only one cys residue could have a beneficial effect. Such genetic modifications could reduce the percentage of dead form with recourse to low temperature production methods.

Example 5

Deletion of Cystine Bridges to Correct Folding Problems

Typically, it is very difficult to define the folding pathways utilized by a protein to get to the final correct form. Nonetheless, some disulfide bridges in the TNF receptor family are unusual and may not be needed for the final folded state. These bridges are good candidates for mutagenesis. One such bridge in the third domain of LTβR-Ig was removed by conventional site directed mutagenesis of cysteines 101 and 108 to alanines (using the numbering from the sequence defined in Ware et al, 1995) led to an improved ratio of dead/live material as evidenced by SDS-PAGE. With wild type LTβR-Ig typically shows the presence of 50 and 5% dead form when produced at 37 and 28° C. respectively. The mutant form with the one cystein disulfide bridge deleted had 20 and 5% dead form when produced at these temperatures.

Example 6

Use of Lower Temperatures to Improve the Quality of a Preparation of HVEM-Ig

Herpes virus entry mediator (HVEM) is a TNF family receptor related to the LTβR and binds tightly to the ligand LIGHT tightly and weakly to the ligand lymphotoxin-a (LTa) (Mauri et al, 1998). Human HVEM was prepared as a Ig fusion protein by PCR amplification of the extracellular domain and fused to the human IgG1 CH2 and CH3 region as described for LTβR-Ig (Crowe et al, 1994). The construct was inserted into a vector called CH269 (Chicheportiche et al, 1997) for transient expression in the human embryonic kidney cell line 293 with high copy vector expression using the EBNA system (293-E cells). Supernatents were collected and HVEM-Ig purified using ProteinA affinity chromatography and low pH elution. Recombinant LTα was prepared from insect cells as described (Browning et al, 1996a). Recombinant soluble human LIGHT was prepared by PCR amplification of the entire cDNA using RNA from activated II23 cells yielding the coding region of the sequence described by Mauri et al, 1998. The receptor binding domain of LIGHT was amplified by PCR and fused onto the alpha mating factor leader sequence and expressed essentially as described for other related proteins (Browning et al, 1996). A FLAG tag and $(G_4S)_3$ spacer amino acid sequences were inserted between the leader and the receptor binding domain such that the secreted LIGHT would possess a N-terminal FLAG sequence. The construct encoded the following molecule:

"MRFPSIFTAVLFAASSALAAPVNTTTEDETAQIPAEAVIGYSDLEGDFD

VAVLPFSNSTNNGLLFINTTIASIAAKEEGVSLEKR..EADYKDDDDNGG

GSGGGSGGGSKELNPAAHLTGANSSLTGSGGPLLWETQLGLAFLRGLSYH

DGALVVTKAGYYYIYSKVQLGGVGCPLGLASTITHGLYKRTPRYPEELEL

LVSQQSPCGRATSSSRVWWDSSFLGGVVHLEAGEEVVVRVLDERLVRLRD

GTRSYFGAFMV"

where the two dots indicates the expected N-terminus of the mature protein which could be further processed by removal of the next two amino acids (EA). The protein was purified from the supernatant by affinity chormatography over an anti-FLAG mAb column and elution with either low pH or calcium chelation. Full length LIGHT was also inserted into a vector CH269 for expression on the surface of 293-E cells as described (Chicheportiche et al, 1997). FACS binding methods for the detection of receptor-Ig to cell surfaces and BIAcore methods for measuring the binding of soluble ligands to immobilized receptor-Ig have been described (Mackay et al, 1997). The BIAcore technology yields real time measurements of protein bound to the chips (i.e. the receptor).

CHO cells expressing HVEM-Ig were grown to confluency at 37 C in roller bottles using growth media supplemented with 10% FBS. When the cells reached confluence, the spent media was exchanged with fresh growth media and the cultures were incubated at 37, 32 and 28 C. The 28 and 32 C cultures were harvested once a week, the 37 C culture every 4 days. The secreted HVEM-Ig was purified using Protein A affinity chromatography as described. The purified preparations were stored at −70 C until analyses. When HVEM-Ig was produced at 28, 32 and 37° C. and purified, all the preparations behaved similarly on SDS-PAGE analysis (FIG. 10) suggesting that large alterations in the protein did not occur. Therefore, if aberrant folding/disulfide bridging occurred, it was either intra-arm or occurred close to the hinge region of the Fc domain, i.e. inter-arm bridging and hence did not appreciably affect the overall shape of the molecule in SDS-PAGE. The ability of the receptor-Ig to bind to LIGHT expressed on 293-E cells or LIGHT on activated II23 cells was assessed in FACS binding assays (FIG. 11). On both cell types, the ability of HVEM-Ig to bind cell surface ligand was improved roughly 2-3 fold upon expression at 32 C. Using BIAcore technology, it was observed that when BIAcore chips were loaded with HVEM-Ig to similar levels (RU values reflect amount of protein on the chip), HVEM-Ig produced at lower temperatures bound more ligand than proteins produced at the higher temperatures (FIG. 12). This result was obtained whether LIGHT or LTα was the ligand. The BIAcore binding curves show the realtime on and off binding events and it can be seen that the binding events were similar regardless of the production temperature. Therefore, a portion of the preparation is effectively dead and this proportion is minimized by lower production temperatures. We speculate that the lower temperature has corrected an aberrant folding problem and improved the percentage of live molecules even though we cannot directly observe the fraction of dead molecules. Affinity chromographic techniques as outlined above could serve to resolve the live/dead forms following optimization of the preparation by lowered growth temperatures and or mutagenesis of various cysteines either in the hinge or in the receptor itself to prevent incorrect folding.

Example 7

Generic Schemes to Minimize Dead Forms of other TNF-Family Receptor-Ig Fusion Proteins Most receptors of the TNF family have been prepared as fusion protein constructs with immunoglobulin-Fc domains:

|  | Reference |
| --- | --- |
| p55 TNF-R | (Loestcher et al, 1991, Marsters et al, 1992; Ashkenazi et al, 1991) |
| p75 TNF-R | (Mohler et al, 1993) |
| LTβ-R | (Crowe et al, 1994) |
| Fas | (Suda et al, 1993) |
| CD27 | (Goodwin et al, 1993) |
| CD30 | (Smith et al, 1993) |
| CD40 | (Fanslow et al, 1992) |
| Ox40 | (Baum et al, 1994) |
| 4-1BB | (Alderson et al, 1994) |
| HVEM | (Mauri et al, 1998) |

In several cases, most notably, Fas-Ig and CD40-Ig e.g. Fanslow et al, 1992, the chimeras are poorly active relative to the soluble Fc forms of the two TNF receptors. It is possible that some of these preparations are mixtures of live and dead forms in varying ratios. A dead form refers simply to a molecule that binds with a affinity substantially (10-1000 fold) lower than the live form, i.e. it may not be completely lack binding activity, but instead has a reduced affinity for ligand relative to the high affinity form found on cells naturally. Abberant inter-receptor arm or intra-receptor arm disulphide linkages may occur leading to a less active protein.

With any of these receptors or other as yet undefined receptors, a panel of anti-receptor mAbs would be prepared by conventional technologies. Those antibodies able to block the binding of the ligand to the receptor preferably as assessed using a ligand binding assay to the native receptor on a cell surface (although other methods using recombinant receptor forms may suffice) would be used to form affinity columns. The preparation of the mixture of live and dead receptor-Fc forms would be passed over the column and the flow through collected. The material that bound to the column would be eluted with a low pH buffer (typically pH 2.5 to 4.0) immediately neutralized. The two fractions would be bound to either cells in a FACS binding assay (or any other standard binding format) or ligand at varying protein concentrations. Some of these mAbs will selectively bind to the live form and a difference between the concentration needed to get 50% binding of the flow through vs eluate will be seen. This result marks that mAb as a demarcating mAb. The ratio of the protein in the eluate to the flow through will indicate the percent live form in the preparation.

These mAbs thus identified can be used to affinity purify the live form. Moreover, their use in various immunoassay formats can be used to optimize for expression of the correct form of the desired receptor-Fc form. The assay can further be used in conjunction with other conventional purification methods to find methods that would purify the active form of the receptor without resort to affinity techniques. Using these Abs to delineate live and dead forms, the culture temperature could be optimized and chromatographic methods developed to enrich for the live form. Alternatively, HIC column methods could be exploited to separate live and dead forms and using this method, culture conditions could be optimized Likewise, these assays would form the basis for cysteine mutagenesis of the receptor portion to define problem disulfide bonds which upon removal would yield functionally active material.

As many of these receptors will have application as therapeutic agents in human disease and one will want to put only properly folded forms into a patient, these methods for both defining the preparation and removing poor binding forms will have utility.

It will be apparent to those skilled in the art that various modifications and variations can be made in the methods of the present invention without departing from the spirit or scope of the invention. Thus, it is intended that the present invention cover the modifications and variations of this invention provided that they come within the scope of the appended claims and their equivalents.

TABLE I

Summary of Anti-LT-b-R mAbs
HT29 Cytotoxicity

| mAb Name | cell Staining | Blocking Receptor Binding[a] | mAb Soluble Immobilized on Plastic[b] | Soluble mAb alone | mAb with LTa1/b2 | Receptor Band Precipitated[f] | mAb Group[g] |
| --- | --- | --- | --- | --- | --- | --- | --- |
| BDA8 | +++ | +++ | ++ | +/− | ---[c] | upper | I |
| AGH1 | +++ |  | +++ | +/− | --- | upper | I |
| BCG6 | +++ | ++ | +++ | +/− | +/− | both | II |
| BHA10 | +++ | +++ | +/−[e] | +/− | +/− | nd | II |
| BKA11 | +++ | +/− | +++ | − | +++[d] | both | III |

TABLE I-continued

Summary of Anti-LT-b-R mAbs HT29 Cytotoxicity

| mAb Name | cell Staining | Blocking Receptor Binding[a] | mAb Soluble Immobilized on Plastic[b] | Soluble mAb alone | mAb with LTa1/b2 | Receptor Band Precipitated[f] | mAb Group[g] |
|---|---|---|---|---|---|---|---|
| CDH10 | +++ |  | +++ | +/− | +++ | nd | III |
| CBE11 | +++ | nd | +++ | +/− | − | both | IV |

[a]Assay assessed whether antibody blocks binding of soluble receptor to activated II-23. nd = not done.
[b]Goat anti-mouse Fc coated plate, captured anti-receptor mAb, HT29s plus IFNg.
[c]Blocks
[d]Potentiates
[e]Variable, some partial inhibition in some assays, none in others.
[f]Receptor form precipitated using mAb plus KappaLock system.
[g]Groups were defined on the basis of the data in this table plus epitope mapping done using BIAcore technology.

TABLE II

Expression of LTβR-Ig constructs in CHO cells cultured at different culture temperatures.

| Construct | Fermentation Temperature ° C. | Expression mg/L[a] | % Inactive Components[b] |
|---|---|---|---|
| LTβR05 | 37 | 6 | 50 |
|  | 32 | 12 | 17 |
|  | 28 | 20 | 10 |
| LTβR09 | 37 | 10 | 50 |
|  | 32 | — | — |
|  | 28 | 76 | 6 |

[a]The expression level was assessed using Protein A affinity chromatography.
[b]The amount of inactive components present in the LTβR-Ig preparation was assessed after Protein A affinity purification using the analytical HIC method.

TABLE III

DME/HAM's F-12 Growth Media Supplements

| Component | Amount in 1 L growth media[a] |
|---|---|
| Fetal Bovine Serum | 100 ml |
| Glucose | 1.85 g |
| Ammonium bicarbonate | 2.2 g |
| Streptomycin | 140 mg |
| Gentamycin | 50 mg |
| Ethanolamine (1 M stock) | 0.1 ml |
| Lipoic acid | 91.2 mg |
| Linoleic acid | 38.4 mg |
| Triiodo-L-Thyronine | 0.2 mg |
| Ex-Cyte VLE (Bayer) | 1 ml |
| Bovine Insulin | 10 mg |
| Bovine Transferrin | 10 mg |
| Bovine Serum Albumin | 50 mg |
| Pluronic F-68 | 1 g |
| Cysteine | 82 mg |
| Methionine | 34 mg |
| Serine | 52 mg |
| Valine | 105.6 mg |
| Glycine | 50 mg |
| Aspartic Acid | 24.4 mg |
| Proline | 52.2 mg |

[a]Components are mixed with the base media powder and the volume is then brought to 1 L. The pH of the media is adjusted to 7.20 ñ 7.25 using 50% HCl.

REFERENCES

Aggarwal, B. and Natarajan, K. (1996) *Eur. Cytokine Rev.* 7:93
Alderson, M. R. et al. (1994) *Eur J Immunol* 24, 2219-27
Ashkenazi, A. et al. (1991) *Proc Natl Acad Sci USA* 88, 10535-9
Banner, D. W. et al (1993) *Cell* 73, 431-445
Baum, P. R. et al. (1994) *Embo J* 13, 3992-4001
Bazzoni, F. and Beutler, B. (1996) *New England J. Med.* 334:1717.
Browning, J. L. et al. (1995) *J. Immunol.* 154, 33-46
Browning, J. et al, (1996) *J. Exp. Med.* 183, 867-878
Browning, J. L. et al. (1996a) *J. Biol. Chem.* 271, 8618-8628
Bucay, N. et al. (1998) *Genes and Development* 12:1260
Chaplin, D. and Fu, Y-X. (1998) *Current Opinion in Immunology* 10, 289-297
Chiceportiche, Y. et al (1997) *J. Biol. Chem.* 272, 32401-32410
Corcoran, A. et al (1994) *Eur. J. Biochem.* 223, 831-840
Crowe, P. D. et al. (1994) *Science* 264, 707-10
Eason, J. D. et al. (1996) *Transplantation* 61:224.
Eggermont, A. M. et al. (1996) *J. Clin. Oncology* 14:2653
Fanslow, W. C. et al. (1992) *J Immunol* 149, 655-60
Feldmann, M. et al. (1997) *Ann. Immunol.* 64:283-350.
Goodwin, R. G. et al. (1993) *Cell* 73, 447-56
Green, D. and Ware, C. F. (1997) *Proc. Natl. Acad. Sci USA* 94:5986
Harrop, J. A., et al, (1998) *J. Biol. Chem.* 273:27548.
Loetscher, H. et al. (1991) *J Biol Chem* 266, 18324-9
Mackay, F. et al. (1998) *Gastroenterology* 115: 1484-1475
Mackay, F and Browning, J. (1998) *Nature* 395:26
Mackay, F. et al. (1997) *Eur J Immunol* 27, 2033-42
Marsters, S. et al (1992) *J. Biol. Chem.* 267, 5747-5750
Mauri, D. N. et al. (1998) *Immunity* 8, 21-30
Mohler, et al. (1993) *J. Immunol* 151, 1548-61
Naismith, J. et al (1996) *J. Mol. Recognition* 9, 113-117
Rennert, P. D. et al. (1996) *J Exp Med* 184, 1999-2006
Rennert, P. D., Browning, J. L., and Hochman, P. S. (1997) *Int Immunol* 9, 1627-39
Simmonet, W. S. et al. (1997) *Cell* 89:309.
Smith, C. A., Farrah, T., and Goodwin, R. G. (1994) *Cell* 76, 959-62
Smith, C. A. et al. (1993) *Cell* 73, 1349-60
Suda, T., Takahashi, T., Golstein, P., and Nagata, S. (1993) *Cell* 75, 1169-78
Van Dullemen, H. M. et al. (1995) *Gastroenterology* 109:129
Ware, C. F. et al. (1995) *Current topics in Microbiology and Immunology* 198, 175-218

What is claimed is:

1. A method for increasing expression of active tumor necrosis factor (TNF) receptor family member-Ig Fc fusion proteins and minimizing expression of inactive TNF receptor family member-Ig Fc fusion proteins comprising culturing a mammalian host cell transformed with DNA molecule encoding a desired TNF receptor-Ig fusion protein in a mammalian cell culture having a minimum temperature of about 27° C. to a maximum temperature of less than or equal to 32° C., wherein the transformed host cell is first cultured at a temperature of about 33° C. to about 37° C. for a period of time sufficient to allow growth of said host cell, and wherein the active TNF receptor family member is involved in immune regulation and comprises 2-4 copies of canonical TNF family cysteine-rich domains.

2. The method of claim 1, wherein the maximum temperature is about 30° C.

3. The method of claim 1, wherein the maximum temperature is about 32° C.

4. The method of any one of claims 1-3, wherein the TNF receptor family member is a lymphotoxin-β receptor, TNFR-55, TNFR-75, HVEM or a ligand-binding portion thereof.

5. The method of claim 4, wherein the TNF receptor family member is a lymphotoxin-β receptor or a ligand-binding portion thereof.

6. The method of any one of claims 1-3, further comprising the step of recovering the active TNF receptor family member-Ig Fc fusion proteins from the culture.

7. The method of claim 6, wherein the active TNF receptor family members are recovered by hydrophobic interaction chromatography.

8. The method of claim 6, wherein the active TNF receptor family member-Ig Fc fusion proteins are recovered based on their ability to bind an antibody that binds directly to the ligand binding region of the TNF receptor family member and exclusively recognizes the active form of the TNF receptor family member-Ig Fc fusion protein.

9. The method of claim 1, wherein the mammalian host cell is a CHO cell.

10. The method of claim 1, wherein the Ig Fc region is human.

11. The method of claim 1, wherein the Ig Fc region is of an IgG1 isotype.

12. A method for increasing the expression of active TNF receptor family member-Ig Fc fusion proteins and minimizing expression of inactive TNF receptor family member-Ig Fc fusion proteins comprising culturing a mammalian host cell transformed with DNA molecule encoding a desired TNF receptor-Ig fusion protein in a mammalian cell culture having a minimum temperature of about 27° C. to a maximum temperature of less than or equal to 32° C. and recovering the active TNF receptor family member-Ig Fc fusion proteins from the culture, wherein the transformed host cell is first cultured at a temperature of about 33° C. to about 37° C. for a period of time sufficient to allow growth of said host cell, and wherein the active TNF receptor family member is involved in immune regulation and comprises 2-4 copies of canonical TNF family cysteine-rich domains.

13. The method of claim 12, wherein the maximum temperature is less than or equal to 30° C.

14. The method of claim 12, wherein the maximum temperature is about 32° C.

15. The method of any one of claims 12-14, wherein the TNF receptor family member is a lymphotoxin-β receptor, TNFR-55, TNFR-75, HVEM or a ligand-binding portion thereof.

16. The method of claim 15, wherein the TNF receptor family member is a lymphotoxin-B receptor or a ligand-binding portion thereof.

17. The method of claim 12, wherein the active TNF receptor family member-Ig Fc fusion proteins are recovered by hydrophobic interaction chromatography.

18. The method of claim 12, wherein the active TNF receptor family member-Ig Fc fusion proteins are recovered based on their ability to bind an antibody that binds directly to the ligand binding region of the TNF receptor family member and exclusively recognizes the active form of the TNF receptor family member-Ig Fc fusion protein.

19. The method of claim 12, wherein the mammalian host cell is a CHO cell.

20. The method of claim 12, wherein the Ig Fc region is human.

21. The method of claim 12, wherein the Ig Fc region is of an IgG1 isotype.

22. The method of claim 1 or 12, wherein the active TNF receptor family member comprises 3-4 copies of canonical TNF family cysteine-rich domains.

23. The method of claim 1 or 12, wherein the transformed host cell is first cultured at a temperature of about 37° C. for the period of time sufficient to allow growth of said host cell.

24. A method for increasing expression of active LTβR-Ig Fc fusion proteins and minimizing expression of inactive LTβR-Ig Fc fusion proteins comprising culturing a mammalian host cell transformed with a DNA molecule encoding an LTβR-Ig fusion protein in cell culture having a minimum temperature of about 27° C. and a maximum temperature of less than or equal to 32° C. and isolating the active LTβR-Ig Fc fusion proteins from the culture medium using hydrophobic interaction chromatography, wherein the transformed host cell is first cultured at a temperature of about 33° C. to about 37° C. for a period of time sufficient to allow growth of said host cell.

25. The method of claim 24, wherein the host cell is a CHO cell.

26. The method of claim 24 or 25, wherein the transformed host cell is first cultured at a temperature of about 37° C. for the period of time sufficient to allow growth of said host cell.

\* \* \* \* \*